(12) United States Patent
Chiefari et al.

(10) Patent No.: US 6,642,318 B1
(45) Date of Patent: Nov. 4, 2003

(54) POLYMERIZATION PROCESS WITH LIVING CHARACTERISTICS AND POLYMERS MADE THEREFROM

(75) Inventors: John Chiefari, Victoria (AU); Roshan Tyrrel Mayadunne, Victoria (AU); Graeme Moad, Victoria (AU); Ezio Rizzardo, Victoria (AU); San Hoa Thang, Victoria (AU)

(73) Assignees: E. I. du Pont de Nemours and Company, Wilmington, DE (US); Commonwealth Scientific and Industrial Research Organization, Victoria (AU)

( * ) Notice: Subject to any disclaimer, the term of this patent is extended or adjusted under 35 U.S.C. 154(b) by 0 days.

(21) Appl. No.: 09/581,953

(22) PCT Filed: Dec. 11, 1998

(86) PCT No.: PCT/US98/26428

§ 371 (c)(1),
(2), (4) Date: Jun. 16, 2000

(87) PCT Pub. No.: WO99/31144

PCT Pub. Date: Jun. 24, 1999

Related U.S. Application Data

(60) Provisional application No. 60/068,074, filed on Dec. 18, 1997, provisional application No. 60/069,981, filed on Dec. 18, 1997, and provisional application No. 60/068,157, filed on Dec. 18, 1997.

(51) Int. Cl.[7] .............................................. C08F 251/00
(52) U.S. Cl. ....................... 525/261; 525/244; 525/260; 526/193; 526/217; 526/219.6; 526/204; 526/222; 526/262; 526/288
(58) Field of Search ................................. 526/193, 217, 526/219.6, 204, 222, 262, 288; 525/244, 260, 261

(56) References Cited

U.S. PATENT DOCUMENTS

| | | |
|---|---|---|
| 5,264,530 A | 11/1993 | Darmon et al. |
| 5,362,826 A | 11/1994 | Berge et al. |
| 5,830,966 A | 11/1998 | Thang et al. |

FOREIGN PATENT DOCUMENTS

| | | |
|---|---|---|
| WO | WO 96/15157 | 5/1996 |
| WO | WO 98/01478 | 1/1998 |

OTHER PUBLICATIONS

Moad et al., The Chemistry of Free Radical Polymerization, Pergamon, London, 1955, pp. 53–95.
Moad et al., The Chemistry of Free Radical Polymerization, Pergamon, London, 1955, pp. 162–186.
Moad et al., The Chemistry of Free Radical Polymerization, Pergamon, London, 1955, pp. 337–339.
Greszta et al., Living Radical Polymerization. 1. Possibilities and Limitations Macromolecules 1994, 27, 638–644.
Cacioli et al., Copolymerization of ω–Unsaturated Oligo–(Methyl Methacrylate): New Macromonomers, J. Macromol. Sci.–Chem., A23(7), 839–852 (1986).
Quirk et al., Experimental Criteria for Living Polymerisations, Polymer International, 27 (1992) 359–367.
Walter et al., An Improved Preparation of Vinylogous Thiocarboxamides, Synthesis, 941–2 (1979).
Timokhina et al., 3–Alkylthio–2–Cycloalkene–1–Thiones, Zh. Org. Khim, 14, 2057–8 (1979).
Muller et al., Kinetic Analysis of "Living" Polymerization Processes Exhibiting Slow Equilibria. 1. Degenerative Transfer (Direct Activity Exchange between Active and "Dormant" Species). Application to Group Transfer Polymerization, Macromolecules, 1995 pp. 4326–4333.
Niwa et al., Molecular Design of Block and Graft Copolymers by Vinyl–substituted Xanthates, Makromol. Chem. 189, 2187–2199 (1988).
Otsu et al. Synthesis, Reactivity, and Role of 4–Vinylbenzyl N,N–Diethyldithiocarbamate as a Monomer–Iniferter in Radical Polymeriation, Macromolecules 1986, 19, 287–290.
Otsu et al., Features of Living Radical Polymerization of Vinyl Monomers in Homogeneous System Using N,N–Diethyldithiocarbamate Derivatives as Photoiniferters, Eur. Polym. J., vol. 31, No. 1, pp 67–78, 1995.
Greenley, Free Radical Copolymerization Reactivity Ratios, Polymer Handbook, 3rd Edition Wiley, NY 1989—II/153–II/266.
Chemical Abstracts, vol. 74, No. 17, Apr. 26, 1971, Abstract No. 87665v, XP–002101249 & JP 45034804 (Meiji Confectionary Co., Ltd.) Nov. 4, 1970.
Chemical Abstracts, vol. 72, No. 11, Abstract No. 53948, XP–002101250 & Vakamori et al., Arg. Biol. Chem. 1969, vol. 33, No. 12, pp. 1691–1699.
Chemical Abstracts, vol. 125, No. 21, Nov. 18, 1996, Abstract No. 276423, XP–002101251 & Quiclet–Sire et al., J. Am. Chem. Soc., vol. 118, No. 38, 1996, pp. 9190–9191.
Copy of the International Search Report, International Application No. PCT/US98/26428.

*Primary Examiner*—Helen L. Pezzuto
(74) *Attorney, Agent, or Firm*—Sudhir G. Deshmukh

(57) ABSTRACT

A free radical polymerization process suitable for synthesizing polymers is disclosed. The process utilizes novel sulfur based chain transfer agents and is widely compatible over a range of monomers and reaction conditions. Novel polymers having low polydispersity and predictably specific polymer architecture and molecular weight are produced by the process. The polymers produced by the process are suitable for use as binders in automotive OEM and refinish coatings.

40 Claims, No Drawings

POLYMERIZATION PROCESS WITH LIVING CHARACTERISTICS AND POLYMERS MADE THEREFROM

This application is a 35 U.S.C. §371 of PCT/US98/26428 filed on Dec. 11, 1998, which claims the benefit of U.S. Provisional Nos. 60/068,074, 60/069,981 and 60/068,157 all filed on Dec. 18, 1997.

BACKGROUND OF THE INVENTION

The present invention generally relates to a free radical polymerization process and particularly relates to a free radical polymerization process utilizing chain transfer agents (CTAs) and to polymers made therefrom.

There is increasing interest in developing polymerization processes that can be predictably controlled to produce polymers having specifically desired structures. One of the means for achieving such results is through a process of living polymerization. Such a process provides a higher degree of control during the synthesis of polymers having predictably well defined structures and properties as compared to polymers made by conventional polymerization processes.

Certain xanthate and dithiocarbamate derivatives of the following formula 1:

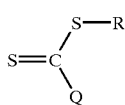 (1)

where Q=O(alkyl) or N(alkyl)$_2$, respectively have been shown to confer some of the characteristics of living polymerization when used as photoinitiators in polymerization processes (see for example Otsu et al., U.S. Pat. No. 5,314,962). Such a process where radicals are generated by direct photolysis of the xanthate or dithiocarbamate derivative do not form part of this invention. See also Niwa et al. (*Makromol. Chem.*, 189, 2187 (1988)) and Otsu et al. (*Macromolecules* 19, 287 (1986)).

Free radical polymerizations in the presence of chain transfer agents (CTAs) represented by formula 1 (where Q=Z' and R are as defined herein) have been disclosed by Le et al. in Int. Patent Application WO 98/01478, which discloses, that since dithiocarbamate and xanthate derivatives disclosed therein have very low transfer constants they are therefore ineffective in conferring living characteristics on a free radical polymerization. However, we have surprisingly found that by appropriate selection of substituents (Q) or the monomer these agents have high chain transfer constants and are effective in conferring living characteristics to a free radical polymerization. The CTAs of the present invention can also advantageously introduce novel end group functionalities into the resulting polymers.

Other process is disclosed in EP 0592 283 A1. The process is directed to synthesizing hydroxylated telechelic polymers obtained in the presence of thiuram sulfide, which acts as an initiator, chain transfer agent and a termination agent. Such agents are commonly referred to as iniferters.

Another process is disclosed in EP 0286 376 A2. The process is directed to synthesizing ABA type block copolymers through photodecomposition of dithiocarbamate group-contaning polymeric intermediates.

Yet another process is disclosed in EP 0349 232 A2. The process is directed to synthesizing acrylic block copolymers by using an iniferter.

Still another process is disclosed in EP 0449 619 A2. The process is directed to synthesizing adhesives by using radiation curable photoiniferters.

Another process is disclosed in EP 0421 149 A1. The process is directed to synthesizing chloroprene polymers having dithiocarbamate groups at both termini of the chloroprene polymeric chain.

Chem. Abstract 74:87665 Apr. 4, 1971) and JP-B-45034804 disclose thiocarbamate iniferter as a polymerization catalyst.

Another Chem. Abstract 72:53948 Mar. 3, 1970) and Agr. Biol. Chem. (1969), 33 (12), 1691–1699 disclose the use of thiocarbonates as herbicides.

Yet another Chem. Abstract 125:276423 Nov. 11, 1996) and J. Am. Chem. Soc. (1996), 118 (38), 9190–9191 disclose a process for synthesizing deoxygenerated sugar derivatives obtained by heating a variety of carbohydrate xanthate containing electron withdrawing ester groups in cyclohexane.

STATEMENT OF THE INVENTION

The present invention is directed to a process for producing a polymer, said process comprising polymerizing a monomer mix into said polymer in the presence of a source of free radicals and a chain transfer agent having a transfer constant in the range of from 0.1 to 5000, said chain transfer agent having the following formula:

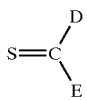

wherein when D is D1 of the following formula:

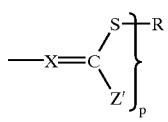

then p is in the range of from 1 to 200, E is Z' and said transfer agent is of the following formula:

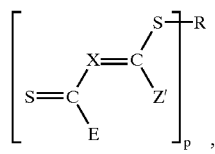

wherein when D is D2 of the following formula:

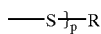

then p is in the range of from 1 to 200, E is E1 or E2 and said transfer agent is of the following formula:

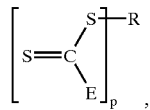

wherein when D is D3 of the following formula:

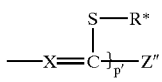

then p' is in the range of from 2 to 200, E is Z, E1 or E2 and said transfer agent is of the following formula:

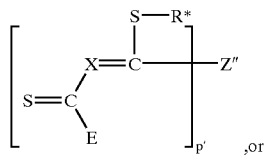

wherein when D is D4 of the following formula:

then E is E3 or E4 and said transfer agent is of the following formula:

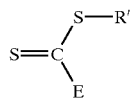

where in all of the above:

R is a p-valent moiety derived from a moiety selected from the group consisting of substituted or unsubstituted alkane, substituted or unsubstituted alkene, substituted or unsubstituted arene, unsaturated or aromatic carbocyclic ring, unsaturated or saturated heterocyclic ring, an organometallic species, and a polymer chain, R. being a free radical leaving group resulting from R that initiates free radical polymerization;

R* and R' are monovalent moieties independently selected from the group consisting of a substituted or unsubstituted alkyl, substituted or unsubstituted alkenyl, substituted or unsubstituted aryl, unsaturated or aromatic carbocyclic ring, unsaturated or saturated heterocyclic ring, substituted or unsubstituted alkylthio, substituted or unsubstituted alkoxy, substituted or unsubstituted dialkylamino, an organometallic species, and a polymer chain, R*. being a free radical leaving group resulting from R* that initiates free radical polymerization;

X is selected from the group consisting of a substituted or unsubstituted methine, nitrogen, and a conjugating group;

Z' is selected from the group consisting of E1, E2, halogen, substituted or unsubstituted alkyl, substituted or unsubstituted alkenyl, substituted or unsubstituted aryl, substituted or unsubstituted heterocyclyl, substituted or unsubstituted alkylthio, substituted or unsubstituted alkoxycarbonyl, substituted or unsubstituted —COOR", carboxy, substituted or unsubstituted —CONR"$_2$, cyano, —P(=O)(OR")$_2$, —P(=O)R"$_2$;

R" is selected from the group consisting of substituted or unsubstituted alkyl, substituted or unsubstituted alkenyl, substituted or unsubstituted aryl, substituted or unsubstituted heterocyclyl, substituted or unsubstituted aralkyl, substituted or unsubstituted alkaryl, and a combination thereof;

Z" is a p'-valent moiety derived from a moiety selected from the group consisting of a substituted or unsubstituted alkane, substituted or unsubstituted alkene, substituted or unsubstituted arene, substituted or unsubstituted heterocycle, a polymer chain, an organometallic species, and a combination thereof;

Z is selected from the group consisting of a halogen, substituted or unsubstituted alkyl, substituted or unsubstituted alkenyl, substituted or unsubstituted aryl, substituted or unsubstituted heterocyclyl, substituted or unsubstituted aryl, substituted or unsubstituted alkoxycarbonyl, substituted or unsubstituted alkylthio, substituted or unsubstituted alkoxycarbonyl, substituted or unsubstituted —COOR", carboxy, substituted or unsubstituted —CONR"$_2$, cyano, —P(=O)(OR")$_2$, —P(=O)R"$_2$;

E1 is a substituent functionality derived from a substituted or unsubstituted heterocycle attached via a nitrogen atom, or is of the following formula:

wherein G and J are independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfinyl, substituted or unsubstituted alkylphosphonyl, substituted or unsubstituted arylsulfonyl, substituted or unsubstituted arylsulfinyl, substituted or unsubstituted arylphosphonyl;

E2 is of the following formula:

wherein G' is selected from the group consisting of substituted or unsubstituted alkyl, substituted or unsubstituted alkenyl, substituted or unsubstituted aryl;

E3 is of the following formula

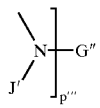

wherein p'" is between 2 and 200, G" is Z" and J' is independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfinyl, substituted or unsubstituted alkylphosphonyl, substituted or unsubstituted arylsulfonyl, substituted or unsubstituted arylsulfinyl, substituted or unsubstituted arylphosphonyl or is joined to G" so as to form a 5–8 membered ring; and E4 is of the following formula

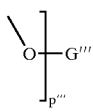

wherein p''' is between 2 and 200 and G''' is Z''.

The present invention is also directed to polymers made by the process of the current invention. One of the embodiment is the polymer is of the following formula:

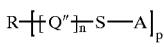

where n is a positive integer in the range of from 1 to 100,000 and wherein A is of the following formula:

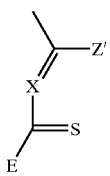

when D is D1 and E is Z';
A is of the following formula:

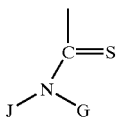

when D is D2 and E is E1; or
A is of the following formula:

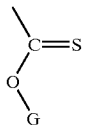

when D is D2 and E is E2; and
and Q'' is a repeat unit derived from a monomer selected from the group consisting of maleic anhydride, N-alkylmaleimide, N-arylmaleimide, dialkyl fumarate, cyclopolymerizable monomer, a ring opening monomer, a macromonomer, a vinyl monomer of the following formula:

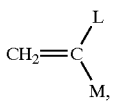

and a combination thereof;
wherein L is selected from the group consisting of hydrogen, halogen, and substituted or unsubstituted $C_1$–$C_4$ alkyl, said alkyl substituents being independently selected from the group consisting of hydroxy, alkoxy, OR'', $CO_2H$, $O_2CR''$, $CO_2R''$ and a combination thereof; and
wherein M is selected from the group consisting of hydrogen, R'', $CO_2H$, $CO_2R''$, COR'', CN, $CONH_2$, CONHR'', $CONR''_2$, $O_2CR''$, OR'', and halogen.

Another embodiment is the polymer comprising a mixture of isomers of the following formula:

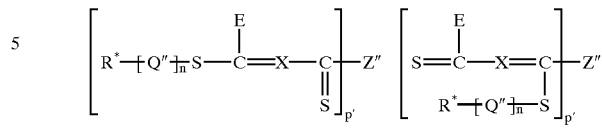

where n is a positive integer in the range of from 1 to 100,000, D is D3, E is Z, E1 or E2.

Still another embodiment is the polymer is of the following formula:

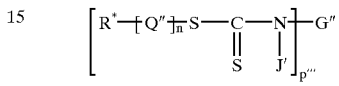

where n is a positive integer in the range of from 1 to 100,000, D is D4, and E is E3.

A further embodiment is the polymer is of the following formulae:

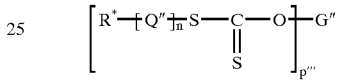

where n is a positive integer in the range of from 1 to 100,000, D is D4, and E is E4.

One of the advantages of the present polymerization system is that by controlling the reaction stoichiometry and the degree of conversion of the monomers into polymer the process produces polymers of predetermined molecular weight and narrow molecular weight distribution over a wide range of monomers and reaction conditions.

Another advantage of the process of the present invention is that by successively adding different monomers to the reaction mixture, block polymers of low polydispersity and desired molecular weight can be produced.

Still another advantage of the process of the present invention is that it is possible to create polymers having complex structures, such as graft, star and branched polymers.

Yet another advantage of the present invention is that it is suitable for carrying out emulsion, solution, or suspension polymerization in either a batch, semi-batch, continuous or feed mode.

Still another advantage of the present invention is that it is suitable for producing waterborne polymers that are water soluble or water dispersible.

Another advantage of the present invention is that it is suitable for producing solvent borne polymers that are solvent soluble or solvent dispersible.

As defined herein:

"Living polymerization" means a process which proceeds by a mechanism whereby most chains continue to grow throughout the polymerization and where further addition of monomer results in continued polymerization (block copolymers can be prepared by sequential monomer addition of different monomers). The molecular weight is controlled by the stoichiometry of the reaction and narrow molecular weight distribution polymers can be produced.

"Radical leaving group" means a group attached by a bond capable of undergoing homolytic scission during a reaction to thereby form a free radical.

"GPC number average molecular weight" (Mn) means a number average molecular weight and "GPC weight average molecular weight" (Mw) means a weight average molecular weight measured by utilizing gel permeation chromatography. A Waters Associates liquid chromatograph equipped with differential refractometer and $10^6$, $10^5$, $10^4$, $10^3$, 500 and 100 Å Ultrastyragel columns was used. Tetrahydrofuran (flow rate of 1.0 mL/min) was used as an eluent. The molecular weights were provided as polystyrene equivalents.

"Polydispersity" (Mw/Mn) means GPC weight average molecular weight divided by GPC number average molecular weight.

"Addition-fragmentation" is a two-step chain transfer mechanism wherein a radical addition is followed by fragmentation to generate new radical species.

"Chain transfer constant" means the ratio of the rate constant for chain transfer to the rate constant for propagation at zero conversion of monomer and CTA. If chain transfer occurs by addition-fragmentation, the rate constant for chain transfer ($k_{tr}$) is defined as follows:

$$k_{tr} = k_{add} \times \frac{k_\beta}{k_{-add} + k_\beta}$$

where $k_{add}$ is the rate constant for addition to the CTA and $k_{add}$ and $k_\beta$ are the rate constants for fragmentation in the reverse and forward directions respectively.

"Polymer chain" means conventional condensation polymers, such as polyesters [for example, polycaprolactone, poly(ethylene terephthalate)], polycarbonates, poly(alkylene oxide)s [for example, poly (ethylene oxide), poly(tetramethylene oxide)], nylons, polyurethanes or addition polymers such as those formed by coordination polymerization (for example polyethylene, polypropylene), radical polymerization (for example poly (meth)acrylates and polystyrenics or anionic polymerization (for example polystyrene, polybutadiene).

"Cyclopolymerizable monomers" means compounds which contain two or more unsaturated linkages suitably disposed to allow propagation by a sequence of intramolecular and intermolecular addition steps leading the incorporation of cyclic units into the polymer backbone. Most compounds of this class are 1,6-dienes such as—diallylammonium salts (e.g., diallyldimethylammonium chloride), substituted 1,6-heptadienes (e.g., 6-dicyano-1,6-heptadiene, 2,4,4,6-tetrakis(ethoxycarbonyl)-1,6-heptadiene) and monomers of the following generic structure

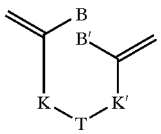

where substituents K, K', T, B, B' are chosen such that the monomer undergoes cyclopolymerization. For example:

B, B' are independently selected from the group consisting of H, $CH_3$, CN, $CO_2Alkyl$, Ph; K, K' are selected from the group consisting of $CH_2$, C=O, $Si(CH_3)_2$, O; T is selected from the group consisting of $C(E)_2$, O, $N(Alkyl)_2$ salts, $P(Alkyl)_2$ salts, P(O)Alkyl. Additional monomers listed in Moad and Solomon "The Chemistry of Free Radical Polymerization", Pergamon, London, 1995, pp 162–170, are also suitable.

"Ring opening monomers" are monomers which contain a suitably disposed carbocyclic or heterocyclic ring to allow propagation by a sequence of intermolecular addition and intramolecular ring opening steps such as those described in Moad and Solomon "The Chemistry of Free Radical Polymerization", Pergamon, London, 1995, pp 171–186.

"Organometallic species" means a moiety containing one or more metal atoms from Groups m and IV of the Periodic Table and transition elements and organic ligands, preferably species, such as, $Si(X)_3$, $Ge(X)_3$ and $Sn(X)_3$ which provide radical leaving groups and initiate polymerization, X being a group discussed later in the specification.

"Heterocyclic" or "heterocyclyl" means a ring structure containing 3 to 18 atoms at least one of which is selected from O, N and S, which may or may not be aromatic. Examples of "heterocyclyl" moieties are pyridyl, furanyl, thienyl, piperidinyl, pyrrolidinyl, pyrazoyl, benzthiazolyl, indolyl, benzofuranyl, benzothiophenyl, pyrazinyl, and quinolyl, optionally substituted with one or more of alkyl, haloalkyl and halo groups.

"Substituent functionality derived from a substituted or unsubstituted heterocycle attached via a nitrogen atom" means the group formed by excising monovalent nitrogen (e.g. >NH) from an appropriate nitrogen containing heterocycle. Said heterocycles include pyrrolidine, pyrrole, indole, imidazole, carbazole, benzimidazole, benzotriazole, piperidine and isatin, all of which may be substituted or unsubstituted. For example, in the case of pyrrole, the substituent functionality is 1,3-butadiene-1,4-diyl, and in the case of pyrrolidine it is butane-1,4-diyl.

Unless specified otherwise, alkyl groups referred to in this specification may be branched or unbranched and contain from 1 to 18 carbon atoms. Alkenyl groups may be branched or unbranched and contain from 2 to 18 carbon atoms. Saturated or unsaturated or carbocyclic or heterocyclic rings may contain from 3 to 18 atoms. Aromatic carbocyclic or heterocyclic rings may contain 5 to 18 carbon atoms.

"Conjugating group" is one which provides orbital overlap between the C=S double bond and the lone pair of the S—R group, in the case of compounds of formula 2 described below, where D=D1, or to the nitrogen lone pair in the case of compounds of the formula 2, where D=D2, E=E1 thereby providing for delocalization of the associated electrons. Examples of such conjugating groups are provided in the subsequent text.

"Substituted" means that a group may be substituted with one or more groups that are independently selected from the group that consisting of alkyl, aryl, epoxy, hydroxy, alkoxy, oxo, acyl, acyloxy, carboxy, carboxylate, sulfonic acid, sulfonate, alkoxy- or aryloxy-carbonyl, isocyanato, cyano, silyl, halo, dialkylamino, and amido. All substituents are chosen such that there is no substantial adverse interaction under the conditions of the experiment.

We have discovered a novel free radical polymerization process and novel polymers produced therefrom. The process is directed to polymerizing a monomer mix in the presence of a source of free radicals and at least one of certain sulfur based CTAs chosen so as to confer living characteristics. By utilizing these CTAs, polymers of controlled molecular weight and low polydispersity can be obtained.

The sulfur based CTAs suitable for use in the present invention have a chain transfer constants in the range of from 0.1 to 5000, preferably in the range of from 1 to 2000 and more preferably in the range of from 10 to 500. If the chain transfer constant of the CTA exceeds the upper limit of the range substantially no polymerization occurs, if it falls below the lower limit it is not possible to produce polymers having low polydispersity. The CTAs of the present invention generally should not copolymerize with monomers during the polymerization process. As a result, low polydispersity polymers based on monosubstituted monomers (e.g., acrylic monomers, styrene) can be made under a wide range of reaction conditions.

The sulfur based CTA suitable for use in the present process is of the formula 2 below:

 (2)

wherein when D is D1 of the following formula 3 below:

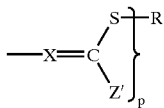 (3)

then p is in the range of from 1 to 200, E is Z' and said transfer agent is of the following formula 4 below:

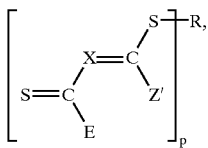 (4)

wherein when D is D2 of the following formula 5 below:

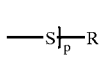 (5)

then p is in the range of from 1 to 200, E is E1 or E2 and said transfer agent is of the following formula 6 below:

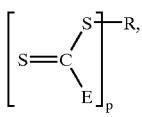 (6)

wherein when D is D3 of the following formula 7 below:

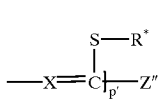 (7)

then p' is in the range of from 2 to 200, E is Z, E1 or E2 and said transfer agent is of the following formula 8 below:

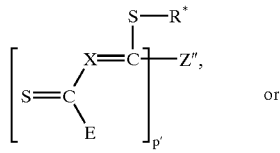 (8)

or wherein when D is D4 of the following formula 9 below:

 (9)

then E is E3 or E4 and said transfer agent is of the following formula 10:

 (10)

where in all of the above:

R is a p-valent moiety derived from a moiety selected from the group consisting of a substituted or unsubstituted alkane, substituted or unsubstituted alkene, substituted or unsubstituted arene, unsaturated or aromatic carbocyclic ring, unsaturated or saturated heterocyclic ring, an organometallic species, and a polymer chain, R. being a free radical leaving group resulting from R that initiates free radical polymerization;

R* and R' are monovalent moieties independently selected from the group consisting of a substituted or unsubstituted alkyl, substituted or unsubstituted alkenyl, substituted or unsubstituted aryl, unsaturated or aromatic carbocyclic ring, unsaturated or saturated heterocyclic ring, substituted or unsubstituted alkylthio, substituted or unsubstituted alkoxy, substituted or unsubstituted dialkylamino, an organometallic species, and a polymer chain, R*. being a free radical leaving group resulting from R* that initiates free radical polymerization;

X is selected from the group consisting of a substituted or unsubstituted methine, nitrogen, and a conjugating group;

Z' is selected from the group consisting of E1, E2, halogen, substituted or unsubstituted alkyl, substituted or unsubstituted alkenyl, substituted or unsubstituted aryl, substituted or unsubstituted heterocyclyl, substituted or unsubstituted alkylthio, substituted or unsubstituted alkoxycarbonyl, substituted or unsubstituted —COOR", carboxy, substituted or unsubstituted —CONR"$_2$, cyano, —P(=O)(OR")$_2$, —P(=O)R"$_2$;

R" is selected from the group consisting of substituted or unsubstituted alkyl, substituted or unsubstituted alkenyl, substituted or unsubstituted aryl, substituted or unsubstituted heterocyclyl, substituted or unsubstituted aralkyl, substituted or unsubstituted alkaryl, and a combination thereof;

Z" is a p'-valent moiety derived from a moiety selected from the group consisting of a substituted or unsubstituted alkane, substituted or unsubstituted alkene, substituted or unsubstituted arene, substituted or unsubstituted heterocycle, a polymer chain, an organometallic species, and a combination thereof;

Z is selected from the group consisting of a halogen, substituted or unsubstituted alkyl, substituted or unsubstituted alkenyl, substituted or unsubstituted aryl, substituted or unsubstituted heterocyclyl, substituted or unsubstituted alkylthio, substituted or unsubstituted alkoxycarbonyl, substituted or unsubstituted —COOR", carboxy, substituted or unsubstituted —CONR"$_2$, cyano, —P(=O)(OR")$_2$, —P(=O)R"$_2$;

E1 is a substituent functionality derived from a substituted or unsubstituted heterocycle attached via a nitrogen atom, or is of the following formula 11:

(11)

wherein G and J are independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfinyl, substituted or unsubstituted alkylphosphonyl, substituted or unsubstituted arylsulfonyl, substituted or unsubstituted arylsulfinyl, substituted or unsubstituted arylphosphonyl; and E2 is of the following formula 12:

(12)

wherein G' is selected from the group consisting of substituted or unsubstituted alkyl, substituted or unsubstituted alkenyl, substituted or unsubstituted aryl;

E3 is of the following formula 13:

(13)

wherein p''' is between 2 and 200, G" is Z" and J' is independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfinyl, substituted or unsubstituted alkylphosphonyl, substituted or unsubstituted arylsulfonyl, substituted or unsubstituted arylsulfinyl, substituted or unsubstituted arylphosphonyl; and E4 is of the following formula 14:

(14)

wherein p''' is between 2 and 200 and G''' is Z'.

The foregoing CTAs are prepared by the following processes:

Vinylogous dithioesters may be prepared in several ways. For example, 3-benzylthio-5,5-dimethylcyclohex-2-ene-1-thione is made by a multi-step process. First, piperidine is condensed with 5,5-dimethylcyclohexane-1,3-dione in the presence of a strong acid to form enaminoketone, which is then converted to a thione derivative. After the addition of benzyl chloride and hydrogen sulfide work-up, the 3-benzylthio-5,5-dimethylcyclohex-2-ene-1-thione is isolated as a purple oil.

The preparation of benzyl 3,3-di(benzylthio)prop-2-enedithioate, another vinylogous dithioester, starts with addition of two moles of carbon disulfide to one mole of the Grignard reagent, such as, methyl magnesium chloride. Treatment with strong base at low temperature followed by addition of benzyl chloride results in the dithioate, which is an orange solid.

The thiocarbonylthio compounds with alpha-nitrogen atoms are synthesized from the corresponding nitrogen compounds. For example, benzyl 1-pyrrolecarbodithioate is prepared by adding pyrrole to sodium hydride suspension in dimethyl sulfoxide followed by the addition of carbon disulfide. Benzyl chloride is added and the product, benzyl 1-pyrrolecarbodithioate, is isolated by extraction with diethyl ether.

The corresponding 2-pyrrolidineone derivative is prepared in a similar manner by starting with pyrrolidone instead of pyrrole.

Benzyl (1,2-benzenedicarboximido)carbodithioate is prepared by carbon disulfide addition to potassium phthalimide. Benzyl chloride is then added to complete the synthesis.

Bis(thiocarbonyl) disulfides masy be the starting material for other dithioate compounds. 2,2'-azobis(2-cyanopropane) is thermally decomposed in the presence of pyrrole N-thiocarbonyl disulfide to produce 2-cyanoprop-2-yl 1-pyrrolecarbodithioate. 2-Cyanobut-2-yl 1-pyrrolecarbodithioate is prepared by the same method using 2,2'-azobis(2-cyanobutane) and pyrrole N-thiocarbonyl disulfide.

Benzyl 1-imidazolecarbodithioate may be prepared by yet another method. Benzyl mercaptan is added to a solution of thiocarbonyldiimidazole in dichloromethane. The compound is then isolated as a yellow oil.

The Xanthate derivatives may be prepared by adding the corresponding halocompound to potassium O-ethyl dithiocarbonate. Therefore, O-ethyl S-(1-phenylethyl)xanthate is made by adding 1-(bromoethyl)benzene to potassium O-ethyl dithiocarbonate. O-Ethyl S-(2-ethoxycarbonylprop-2-yl) xanthate is made by adding 2-bromoisobutyrate to potassium O-ethyl dithiocarbonate, and O-ethyl S-(2-cyanoisopropyl)xanthate is made by adding 2-bromoisobutyronitrile to potassium O-ethyl dithiocarbonate.

Some of the preferred CTAs include the following:

1. The CTA which includes D1 of the formula 15 below:

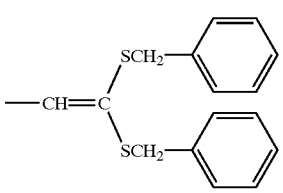
(15)

when E1 is of the formula 16 below:

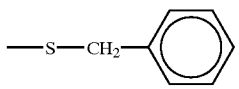 (16)

2. The CTA which includes D2 of the formula 17 below:

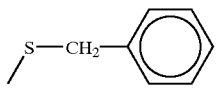 (17)

when E1 is of the formulas 18–20 below:

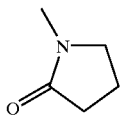 (18)

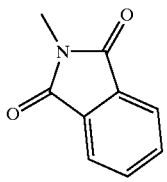 (19)

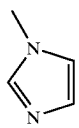 (20)

or E2 is of the formulas 21 or 22 below:

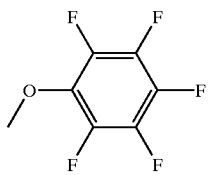 (21)

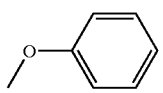 (22)

3. The CTA which includes D2 of the formulas 23 or 24 below:

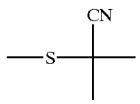 (23)

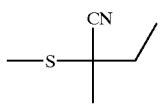 (24)

when E1 is of the formula 25 below:

 (25)

4. The CTA which includes D2 of the formulas 26, 27 or 28 below:

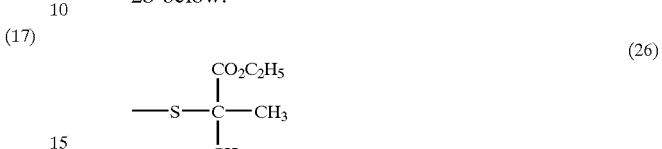 (26)

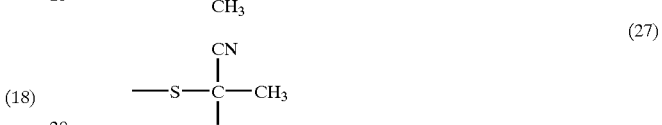 (27)

 (28)

when E2 is of the formula 29 below:

 (29)

If desired, the CTA of the formula 2 further includes a cyclic structure when D is D1 and Z' and E are such that E—C—X=C—Z' forms a ring structure. The bridging functionality forms a bridge between Z' and E. When such as a cyclic structure is present, Z' and E may not be halogen, methyl or carboxy functionality.

One of the CTAs having the bridging functionality is of the following formula 30 below where E, Z'=neopentylene:

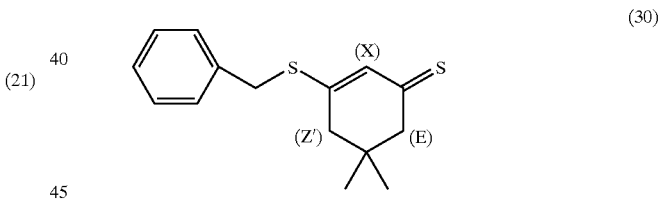 (30)

The source of free radicals suitable for use in the present invention includes those compounds that provide free radicals that add to monomers to produce propagating radicals. Propagating radicals are radical species that have added one or more monomer units and are capable of adding further monomer units.

The amount of the free radical initiator used depends upon the desired polydispersity, molecular weight and polymer structure of the resulting polymer. However, generally less than 10 percent, preferably in the range of from 0.001 to 5 percent of the free radical initiator is used, all percentages being in weight percent based on the total amount of monomer mixture.

The source of initiating radicals may be any suitable method of generating free radicals that provide free radicals that add to monomers to produce propagating radicals. This includes such sources as the thermally induced homolytic scission of a suitable compound(s) (such as peroxides, peroxyesters, or azo compounds), the spontaneous generation from monomer (e.g. styrene), redox initiating systems, photochemical initiating systems or high energy radiation such as electron beam, X- or γ-radiation. The initiating system is chosen such that under the reaction conditions there is no substantial adverse interaction of the initiator or the initiating radicals with the transfer agent under the conditions of the experiment. The initiator should also have the requisite solubility in the reaction medium or monomer mixture.

Examples of suitable sources of free radicals for the process include azo compounds and peroxides such as:

2,2'-azobis(isobutyronitrile), 2,2'-azobis(2-cyano-2-butane), dimethyl 2,2'-azobis(methyl isobutyrate), 4,4'-azobis(4-cyanopentanoic acid), 4,4'-azobis(4-cyanopentan-1-ol), 1,1'-azobis(cyclohexanecarbonitrile), 2-(t-butylazo)-2-cyanopropane, 2,2'-azobis[2-methyl-N-(1,1)-bis(hydoxymethyl)-2-hydroxyethyl]propionamide, 2,2'-azobis[2-methyl-N-hydroxyethyl)]-propionamide, 2,2'-azobis(N,N'-dimethyleneisobutyramidine) dihydrochloride, 2,2'-azobis(2-amidinopropane) dihydrochloride, 2,2'-azobis(N,N'-dimethyleneisobutyramine), 2,2'-azobis(2-methyl-N-[1,1-bis(hydroxymethyl)-2-hydroxyethyl] propionamide), 2,2'-azobis(2-methyl-N-[1,1-bis(hydroxymethyl)ethyl]propionamide), 2,2'-azobis[2-methyl-N-(2-hydroxyethyl)propionamide], 2,2'-azobis(isobutyramide)dihydrate, 2,2'-azobis(2,2,4-trimethylpentane), 2,2'-azobis(2-methylpropane), t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl hyponitrite, or dicumyl hyponitrite.

Free radicals may also be generated thermally from the monomer (e.g. styrene), by photochemistry, from redox initiation systems or by a combination of these methods.

Photochemical initiator systems are chosen to have the requisite solubility in the reaction medium or monomer mixture and have an appropriate quantum yield for radical production under the conditions of the polymerization. Examples include benzoin derivatives, benzophenone, acyl phosphine oxides, and photo-redox systems. Such processes where free radicals are derived by direct photolysis of the compound of formula 2 where D=D2 and E=E1 or E2 are not part of this invention.

Redox initiator systems are chosen to have the requisite solubility in the reaction medium or monomer mixture and have an appropriate rate of radical production under the conditions of the polymerization; these initiating systems may include combinations of the following oxidants and reductants:

oxidants: potassium peroxydisulfate, hydrogen peroxide, t-butyl hydroperoxide.

reductants: iron (II), titanium (III), potassium thiosulfite, potassium bisulfite other suitable initiating systems are described in recent texts. See, for example, Moad and Solomon "The Chemistry of Free Radical Polymerization", Pergamon, London, 1995, pp 53–95.

A monomer mix suitable for use in the present invention may include at least one vinyl monomer of the formula 31 below:

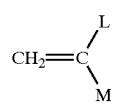

(31)

where L is selected from the group consisting of hydrogen, halogen, and substituted or unsubstituted $C_1$–$C_4$ alkyl, said alkyl substituents being independently selected from the group consisting of OH, OR", $CO_2H$, $O_2CR$", $CO_2R$" and a combination thereof;

where M in the formula 31 is selected from the group consisting of hydrogen, R", $CO_2H$, $CO_2R$", COR", CN, $CONH_2$, CONHR", $CONR"_2$, $O_2CR$", OR", and halogen.

R" is as defined above.

Depending upon the type of polymer desired, the monomer mix may also include the following monomers:

Maleic anhydride, N-alkylmaleimide, N-arylmaleimide, dialkyl fumarate, cyclopolymerizable or a ring opening monomer, or a combination thereof. The monomer mix may also include macromonomers, which are compounds of the formula 31 where L or M is a polymer chain.

The monomers or comonomers of the formula 31 generally include one or more of acrylate and methacrylate esters, acrylic and methacrylic acids, styrene, acrylamide, methacrylamide, acrylonitrile, methacrylonitrile, vinyl esters and mixtures of these monomers, and mixtures of these monomers with other monomers. As one skilled in the art would recognize, the choice of comonomers is determined by their steric and electronic properties. The factors which determine copolymerizability of various monomers are well documented in the art. For example, see: Greenley, R. Z. in Polymer Handbook 3rd Edition (Brandup, J., and Immergut, E. H Eds.) Wiley: New York, 1989 p II/53.

The specific monomers or comonomers of the formula 31 include one or more of the following:

methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), methyl α-hydroxymethyacrylate, ethyl α-hydroxymethyacrylate, butyl α-hydroxymethyacrylate, N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers). p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, isoprene, chloroprene, ethylene and propylene.

Other suitable monomers include cyclopolymerizable monomers such as those disclosed in International Patent Application PCT/AU94/00433 or Moad and Solomon "The Chemistry of Free Radical Polymerization", Pergamon, London, 1995, pp 162–171 and ring opening monomers such as those described in Moad and Solomon "The Chemistry of Free Radical Polymerization", Pergamon, London, 1995, pages 171–186.

The polymer resulting from the process of the present invention is of the following formula 32:

(32)

where n is a positive integer in the range of from 1 to 100,000, preferably in the range of from 5 to 10000 and more preferably in the range of from 10 to 1000. Q" in the formula 32 and the formulas below is a repeat unit derived from a monomer selected the group consisting of maleic anhydride, N-alkylmaleimide, N-arylmaleimide, dialkyl fumarate, cyclopolymerizable monomer, a ring opening monomer, a macromonomer, a vinyl monomer of formula 31 (when Q" will have structure (33)

(33)

and a combination thereof;
wherein L is selected from the group consisting of hydrogen, halogen, and substituted or unsubstituted $C_1$–$C_4$ alkyl, said alkyl substituents being independently selected from the group consisting of OH, OR", $CO_2H$, $O_2CR"$, $CO_2R"$ and a combination thereof;

wherein M is selected from the group consisting of hydrogen, R", $CO_2H$, $CO_2R"$, COR", CN, $CONH_2$, CONHR", $CONR"_2$, $O_2CR"$, OR", and halogen; and R" is as defined above.

A in the formula 32 is of the formula 34 below, when D is D1 and E is Z':

(34)

Thus, when p=1 the resulting polymer will comprise a mixture of the isomers shown in formula 35 below:

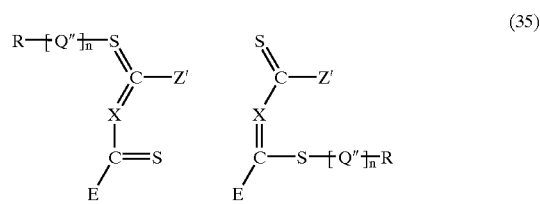

(35)

Alternatively, A is of the formula 36 below when D is D2 and E is E1:

(36)

Thus, when p=1, the resulting polymer is of the formula 37 below:

(37)

In yet another embodiment, A is of the formula 38 below when D is D2 and E is E2:

(38)

Thus, when p=1, the resulting polymer is of the formula 39 below:

(39)

Another type of polymer resulting from the process of invention has the following formula 40 (the product will be a mixture of isomers).:

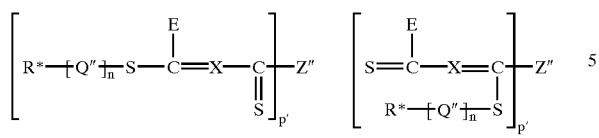

(40)

where n is a positive integer in the range of from 1 to 100,000, and D is D3 and E is Z, E1 or E2.

Still other types of polymer resulting from the process of invention has the formula 41 or 41a:

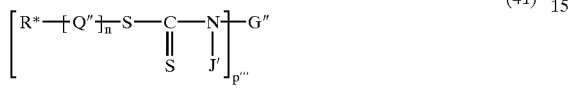

(41)

where n is a positive integer in the range of from 1 to 100,000, and D is D4 and E is E3.

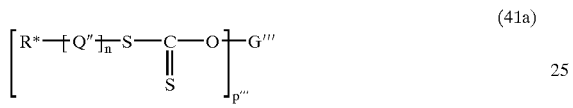

(41a)

where n is a positive integer in the range of from 1 to 100,000, and D is D4 and E is E4.

In the context of the present invention, low polydispersity polymers are those with polydispersities that are significantly less than those produced by conventional free radical polymerization. In conventional free radical polymerization, polydispersities of the polymers formed are typically in the range 1.5 to 2.0 at low monomer conversions in the range of from 0.1% to 10% and are substantially greater in the range of from 2 to 10 at higher monomer conversions in the range of from 10% to 100%. Polymers having low polydispersity in the range of from 1.05 to 1.5 are preferred. Those having the polydispersity in the range of 1.05 to 1.3 are more preferred. Moreover, one of the significant advantages of the process of the present invention is that the foregoing low polydispersity can be maintained even at high monomer conversions of in the range of from 10% to 100%.

However, it should be understood, it is also possible, if desired, to produce polymers with broad, yet controlled, polydispersity or multimodal molecular weight distribution by controlled addition of the CTA over the course of the polymerization process of the present invention.

The invention can be used to narrow the polydispersity of polymers formed in polymerizations that would otherwise produce polymers of broad or very broad polydispersities. In this circumstance a preferred polydispersity is one which is less than that formed in the absence of the CTA.

While not wishing to be limited to any particular mechanism, it is believed that the mechanism of the process is as summarized in Scheme I below. Propagating radicals $P_n\cdot$ are produced by radical polymerization. These can react reversibly with the chain transfer agent RA to form an intermediate radical $P_nA(\cdot)R$ which fragments to give a radical R· (which adds monomer to reinitiate polymerization) and a new transfer agent $P_nA$. This new transfer agent $P_nA$ has similar characteristics to the original transfer agent RA in that it reacts with another propagating radical $P_m\cdot$ to form an intermediate radical $P_nA(\cdot)P_m$ which fragments to regenerate $P_n\cdot$ and form a new transfer agent $P_mA$ which has similar characteristics to RA. This process provides a mechanism for chain equilibration and accounts for the polymerization having living characteristics.

Scheme 1:

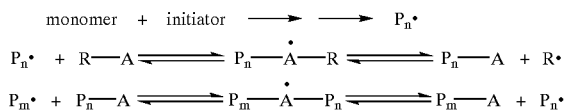

$P_n\cdot$ and $P_m\cdot$ are propagating radicals of chain length n and m respectively. R· is a chain transfer agent derived radical which can initiate polymerization to produce a new propagating radical. RA, $P_nA$ and $P_mA$ are CTAs.

The molecular weight and the polydispersity of the polymer made by the process of the present invention are controlled by one or more of the following:

The polymerization conditions are selected to minimize the number of chains formed from initiator-derived radicals to an extent consistent with obtaining an acceptable rate of polymerization. Termination of polymerization by radical-radical reaction will lead to chains which contain no active group and therefore cannot be reactivated. The rate of radical-radical termination is proportional to the square of the radical concentration. Furthermore, in the synthesis of block, star or branched polymers, chains formed from initiator-derived radicals will constitute a linear homopolymer impurity in the final product. These reaction conditions therefore require careful choice of the initiator concentration and, where appropriate, the rate of the initiator feed.

It is also desirable to choose other components of the polymerization medium (for example, the solvents, surfactants, additives, and initiator) such that they have a low transfer constant towards the propagating radical. Chain transfer to these species will lead to the formation of chains which do not contain the active group.

As a general guide in choosing conditions for the polymerization of narrow polydispersity polymers, the concentration of initiator(s) and other reaction conditions [solvent (s) if any, reaction temperature, reaction pressure, surfactants if any, other additives] should be chosen such that the molecular weight of polymer formed in the absence of the CTA is at least twice that formed in its presence. In polymerizations where radical-radical termination is solely by disproportionation, this equates to choosing an initiator concentration such that the total moles of initiating radicals formed during the polymerization is in the range of 0.000001 times to 0.5 times that of the total moles of CTA. More preferably, conditions should be chosen such that the molecular weight of polymer formed in the absence of the CTA is at least 5-fold that formed in its presence ([initiating radicals]/[CTA]<0.2).

Thus, by varying the ratio of the total number of moles of the CTA to the total number of moles of the free radical initiator added to a polymerization medium, the polydispersity of the resulting polymer is controlled. Thus, by decreasing the foregoing ratio, a polymer of lower polydispersity is obtained and by increasing the ratio, a polymer of higher polydispersity is obtained.

With these provisos, the polymerization process according to the present invention is performed under the conditions typical of conventional free-radical polymerization. Polymerization employing the CTAs of the present invention is suitably carried out with temperatures during the reaction in the range −20° C. to 200° C., preferably in the range 40 to 160° C.

Unlike, a conventional free radical polymerization process, the molecular weight of the resulting polymer by the process of the present invention generally increases in a predictable and linear fashion, and may be estimated in accordance with the following relationship:

$$MW_{prod} = \frac{[\text{Moles of monomer consumed}]}{[\text{moles of CTA}]} \times MW_{mon} + MW_{cta}$$

where $MW_{prod}$ is the number average molecular weight of the isolated polymer, $MW_{mon}$ is the molecular weight of the monomer and $MW_{cta}$ is the molecular weight of the CTA. The foregoing expression applies under reaction conditions where the number of initiator-derived chains is less than 10 percent with respect to total chains and when the added CTA is completely reacted. More complex expressions may be derived to enable prediction of the molecular weight in other circumstances.

By way of illustration, consider the data provided in Examples 19 and 20. A close correspondence is seen between molecular weights calculated according to the above equation and those found experimentally.

| MW prod (found) | fractional conversion | moles monomer consumed | moles CTA | MW prod (calc) |
|---|---|---|---|---|
| 37257 | 0.31000 | 0.017230 | 4.0952e-05 | 36393 |
| 97127 | 0.89000 | 0.049467 | 4.0952e-05 | 104090 |
| 110910 | 0.91000 | 0.050579 | 4.0952e-05 | 106430 |
| 3381.0 | 0.22000 | 0.012228 | 0.00040952 | 2777.9 |
| 5952.0 | 0.47000 | 0.026123 | 0.00040952 | 5695.9 |
| 8762.0 | 0.74000 | 0.041130 | 0.00040952 | 8847.4 |

The process of this invention can be carried out in emulsion, solution or suspension in either a batch, semi-batch, continuous, or feed mode. Otherwise-conventional procedures can be used to produce narrow polydispersity polymers. For lowest polydispersity polymers, the CTA is added before polymerization is commenced. For example, when carried out in batch mode in solution, the reactor is typically charged with CTA and monomer or medium plus monomer. To the mixture is then added the desired amount of initiator and the mixture is heated for a time which is dictated by the desired conversion and molecular weight.

Polymers with broad, yet controlled, polydispersity or with multimodal molecular weight distribution can be produced by controlled addition of the CTA over the course of the polymerization process.

In the case of emulsion or suspension polymerization the polymerization medium will often be predominantly water and the conventional stabilizers, dispersants and other additives can be present.

For solution polymerization, the polymerization medium can be chosen from a wide range of media to suit the monomer(s) being used. For example, aromatic hydrocarbons, such as, petroleum naphtha or xylenes; ketones, such as, methyl amyl ketone, methyl isobutyl ketone, methyl ethyl ketone or acetone; esters, such as, butyl acetate or hexyl acetate; and glycol ether esters, such as, propylene glycol monomethyl ether acetate.

As has already been stated, the use of feed polymerization conditions allows the use of CTAs with lower transfer constants and allows the synthesis of polymers that are not readily achieved using batch polymerization processes. If the polymerization is carried out as a feed system the reaction can be carried out as follows. The reactor is charged with the chosen polymerization medium, the CTA and optionally a portion of the monomer mixture. Into a separate vessel is placed the remaining monomer mixture. The free radical initiator is dissolved or suspended in polymerization medium in another separate vessel. The medium in the reactor is heated and stirred while the monomer mixture+medium and initiator+medium are introduced, for example by a syringe pump or other pumping device. The rate and duration of feed is determined largely by the quantity of solution, the desired monomer/CTA/initiator ratio and the rate of the polymerization. When the feed is complete, heating may be continued for an additional period. Sequential addition of different monomers will give a block or gradient copolymer.

Following completion of the polymerization, the polymer can be isolated by stripping off the medium and unreacted monomer(s) or by precipitation with a non-solvent. Alternatively, the polymer solution/emulsion can be used as such, if appropriate to its application.

The process of the present invention is compatible with a wide variety of monomers and can be used under varied reaction conditions to produce polymers having low polydispersity. By varying the rate of monomer(s) addition or by varying the sequence in which the monomer(s) may be added to the polymerization medium, the process present invention may be used to produce block and multi-block and gradient polymers. By selecting the functionalities desired, an end-functional polymer of specific end functionalities can be readily produced.

Examples of CTAs of the formula 6 which are precursors to graft polymers of formula 32, which include copolymers and/or xanthate or dithiocarbamate derivative of the following formula 42:

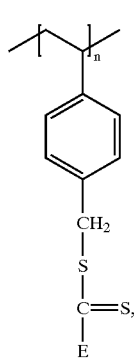

(42)

when in the formula 32, p=n and R is of the following formula 43:

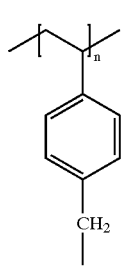

(43)

Examples of CTAs containing functionality attached to a common nucleus are described below.

When in the formula 6 p=2, R=p-xylylene, the CTA is of the formula 44 below:

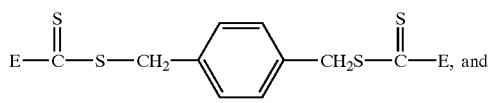
(44)

and when in the formula 10, p'''=2, E=E4, G''' =p-phenylene then the CTA is of the formula 45 below:

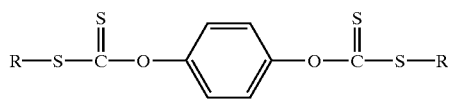
(45)

The compound of the following formula (46) will provide a star polymer, as shown below:

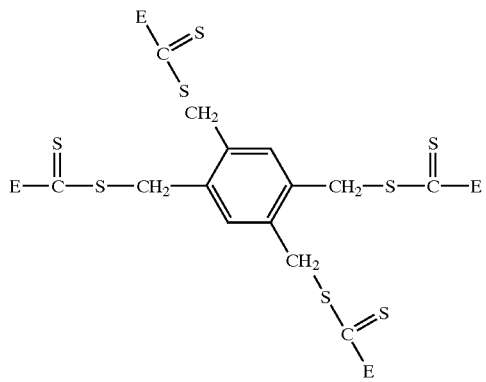
(46)

When in the formula 6, p=4 and R is of the following formula 47 below:

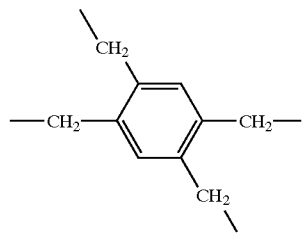
(47)

The polydispersity obtained under a given set of reaction conditions is sensitive to the value of the transfer constant ($C_{tr}$). Lower polydispersities will result from the use of CTAs with higher transfer constants. According to the above mechanism, the chain transfer activities of the reagents (RA, $P_nA$ and $P_mA$) will be determined by the reactivity of the C=S double bond and by the rate of fragmentation and the partitioning of the intermediate radicals between starting materials and products.

Müller et al. have derived relationships which enable polydispersities to be estimated for polymerizations which involve chain equilibration by reversible chain transfer (Miller, A. H. E.; Zhuang, R.; Yan, D.; Litvenko, G. *Macromolecules*, 28, 4326 (1995))

$$M_w/M_n = 1 + 1/C_{tr}$$

Where $C_{tr}$ is the chain transfer constant.

This above relationship should apply to batch polymerizations carried to full conversion in the situation where the number of initiator-radical derived chains is small with respect to total chains and there are no side reactions. This relationship suggests that the transfer constant should be greater than 2 to obtain a polydispersity <1.5 in a batch polymerization.

For a feed polymerization in which the monomer concentration is kept constant by continual replenishment, Miller et al. suggest that the following relationship should hold (Müller, A. H. E.; Litvenko, G., Macromolecules 30, 1253 (1997)):

$$Mw/Mn = 1 + (2/DPn)(1/C_{tr})([M]/[CTA])$$

Where $C_{tr}$ is the chain transfer constant and DPn is the degree of polymerization of the product.

A possible mechanism of the addition-fragmentation step, without reliance thereon, for the case of compounds of the formula 2 where D is D1 is as follows:

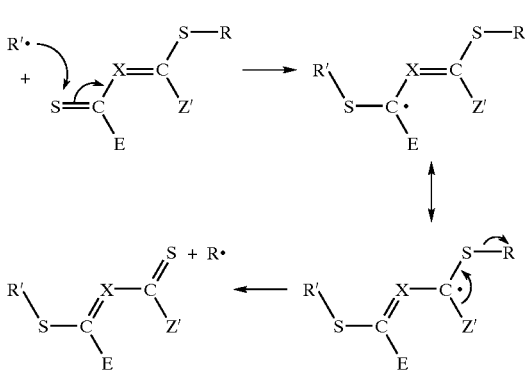

The foregoing proposed mechanism is in accord with experimental observations. According to this mechanism, the X group may in principle be any group which maintains conjugation between the C=S and the S—R groups. Some possible structures are included in the following formulas 48–50:

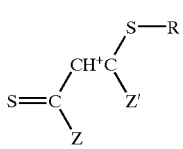
(48)

X = methine

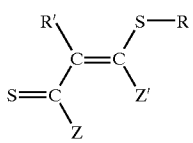
(49)

X = substituted methine

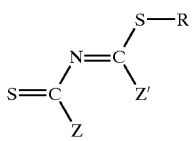
(50)

X = nitrogen

Other examples of CTAs with conjugating groups are of the following formulas 51–53 below:

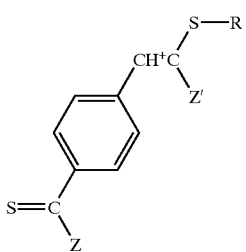

X = para-phenylenemethine

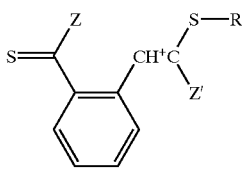

X = ortho-phenylenemethine

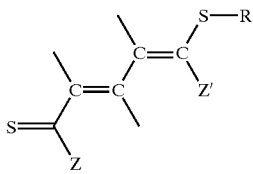

X = allylene

Structures containing multiple alkylthio groups allow the synthesis of polymers of more complex architecture. For example the following compound can give rise to a three arm star 54 as follows:

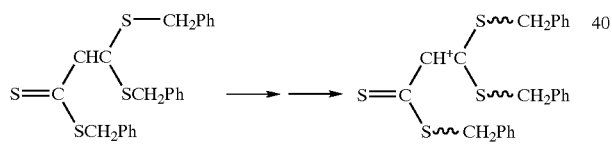

Sequential addition of monomers will give rise to block copolymers.

It will be clear to those skilled in the art that to be effective as a CTA in the present invention, the group R of the CTA must be both a free radical leaving group and a species that initiates free radical polymerization. Leaving group ability is determined both by steric factors and by radical stability. Examples of preferred R groups for the CTA are benzyl derivatives (—CR'''$_2$Ph) and cyanoalkyl derivatives (—CR'''$_2$CN) and other moieties known to the art as free radical leaving groups.

The leaving group ability of R. will also be determined by the nature of the propagating species formed in the polymerization. For example, in styrene polymerization, R is preferably selected from the group consisting of benzyl, 1-phenylethyl, 2-phenylpropyl, 2-(alkoxycarbonyl)prop-2-yl, 2-cyanoprop-2-yl, 2-cyanobut-2-yl, and 1-cyanocyclohexyl. In methyl methacrylate polymerization R is preferrably selected from the group consisting of 2-phenylpropyl, 2-cyanoprop-2-yl, 2-cyanobut-2-yl, and 1-cyanocyclohexyl. In vinyl acetate polymerization R is preferrably selected from the group consisting of 2-(alkoxycarbonyl)prop-2-yl, cyanomethyl, 2-cyanoprop-2-yl, 2-cyanobut-2-yl, and 1-cyanocyclohexyl.

To avoid retardation the R''', substituents should be chosen such that R. gives facile addition to the monomer. In this context, the preferred R''' groups are independently selected from the group consisting of hydrogen and substituted alkyl. The ability of R. to initiate polymerization will be determined by the nature of the monomers used in the polymerization. In polymerization of styrene and methacrylates benzyl derivatives (—CR'''$_2$Ph) and cyanoalkyl derivatives (—CR'''$_2$CN) are effective. However, in vinyl acetate polymerization benzyl derivatives (—CR'''$_2$Ph) are slow to initiate polymerization, and retardation may be observed, but cyanoalkyl derivatives (—CR'''$_2$CN) and the corresponding esters (—CR'''$_2$CO$_2$Alkyl) are effective.

In polymerizations of (meth)acrylates and styrene, we have discovered that dithiocarbamate CTAs (formula 2, D=D2, E=E1) with conjugating or electron withdrawing substituents at the dithiocarbamate nitrogen are substantially more effective than dithiocarbamate derivatives with simple alkyl substituents.

Thus, the preferred groups in E1 for this application are aromatic nitrogen heterocycles where G—N—J forms part of aromatic cyclic group, such as those of the following formulas 55 and 56 below:

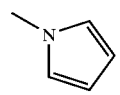

pyrroles

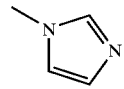

imidazoles and groups in E1 such as cyclic amides where G—N—J forms part of a non-aromatic cyclic group with substituent such as oxo conjugated to nitrogen as in the following formulas 57–59 below:

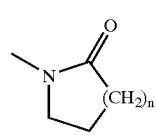

lactam

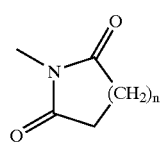

imide

-continued

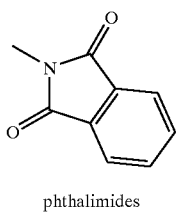

phthalimides (59)

One possible explanation for the greater activity of the above dithiocarbamates is in terms of a higher reactivity of the C=S double bond towards free radical addition. This is attributed to the effect of the conjugating or electron withdrawing substituents giving greater double bond character to the C=S double bond.

In carbamates and amides the N—CO link has partial double bond character as a result of the delocalisation of the non-bonded nitrogen lone pair with the p electrons of carbonyl group (Deslongchamps, P. Stereoelectronic effects in organic chemistry, Pergamon Press, NY, 1983). As a result, the oxygen of the carbonyl group has a partial negative charge. Since sulfur has a higher electron affinity than oxygen, this effect would be expected to be more pronounced in dithiocarbamates.

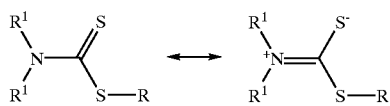

If the nitrogen lone pair participates in an alternate π-system (e.g. the aromatic pyrrole ring) the lone pair will be less available for delocalization into the thiocarbonyl bond resulting in a greater double bond character for the C=S double bond and hence a greater reactivity of the CTA towards radicals.

Similar considerations apply in the case of xanthate esters. We have found that effectiveness of xanthate ester CTAs (formula 2, D=D2, E=E2) in providing low polydispersity polymers in acrylate polymerization increases in the series where G' is —OEt<—OC$_6$H$_5$<C$_6$F$_5$.

The transfer constants of dithiocarbamate and xanthate derivatives (compounds of formula 2 D=D2, E=E1 or E2 repectively) are strongly dependent on the monomer used. Thus dithiocarbamate and xanthate derivatives of formula 2 with D=D2 and E=E1 or E2 wherein G, J, and G' are independently selected from the group consisting of substituted or unsubstituted alkyl, substituted or unsubstituted alkylene, substituted or unsubstituted aryl, substituted or unsubstituted heterocyclyl have relatively low transfer constants in polymerization of methacrylate or styrene monomers and are not effective in giving narrow polydispersity polymers in batch polymerization of such monomers.

However in polymerization of vinyl acetate, vinyl butyrate, vinyl benzoate, vinyl chloride, vinyl bromide, vinyl fluoride, N-vinylpyrolidone, N-vinylcarbazole and similar vinyl monomers these dithiocarbamate and xanthate derivatives (compounds of formula 2, D=D2, E=E1 or E2) have higher transfer constants enabling low polydispersity polymers to be achieved. Preferred CTAs for use with these vinyl monomers include compounds of formula 2 with D=D2 and E=E1 or E2 wherein G, J, and G' are independently selected from the group consisting of substituted or unsubstituted alkyl, substituted or unsubstituted alkylene, substituted or unsubstituted aryl, substituted or unsubstituted heterocyclyl, or when E=E1, G-N-J forms part of a non-aromatic cyclic group.

The invention has wide applicability in the field of free radical polymerization and can be used to produce polymers that are suitable for use in compositions for coatings, including automotive OEM and refinishes, as primers, basecoats, undercoats, overcoats and clear coats. The polymers are also suitable for use in compositions for maintenance finishes for a wide variety of substrates, such as steel, copper, brass and aluminum or non-metallic substrates, such as, wood, leather and concrete.

A coating composition containing the polymer prepared by the process of the present invention may also contain conventional additives, such as, pigments, stabilizers, flow agents, toughening agents, fillers, durability agents, corrosion and oxidation inhibitors, rheology control agents, metallic flakes and other additives. Such additional additives will, of course, depend on the intended use of the coating composition. Fillers, pigments, and other additives that would adversely effect the clarity of the cured coating will not be included if the composition is intended as a clear coating.

Block and star, and branched polymers can be used as compatibilizers, thermoplastic elastomers, dispersing agents, flocculants, surfactants, rheology control agents or as additives to modify the surface properties of bulk polymers and plastics. Additional applications for polymers of the invention are in the fields of imaging, electronics (e.g., photoresists), engineering plastics, adhesives, sealants, paper coatings, printing inks, and polymers in general.

The invention can also be applied to the controlled grafting of polymer chains onto solid polymers or surfaces for the purpose of controlling biocompatibility, biostability, hydrophilicity, hydrophobicity, adhesion or friction.

EXAMPLES

Monomers were purified (to remove inhibitors) and flash distilled immediately prior to use. Degassing was accomplished by repeated freeze-evacuate-thaw cycles. Once degassing was complete ampoules were flame sealed under vacuum and completely submerged in an oil bath at the specified temperature for the specified times. The percentage conversions were calculated gravimetrically.

Examples 1–6 illustrate the synthesis of thiocarbonylthio compounds with an α-nitrogen substituent (dithiocarbamates formula 2, D=D2, E=1)

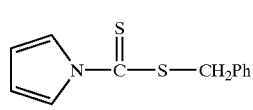

(60)

D = D2, R = benzyl; E = E1 = 1-pyrrolyl

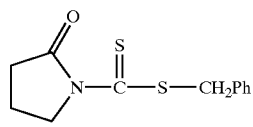

(61)

D = D2, R = benzyl;
E = E1 = 1-(pyrrolidin-2-onyl)

-continued

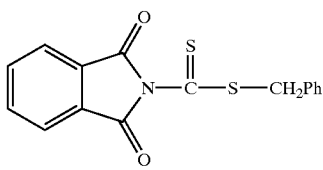

D = D2, R = benzyl;
E = E1 = N-phthalimidyl

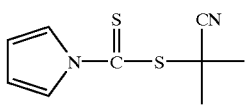

D = D2, R = 2-cyanoprop-2-yl
E = E1 = 1-pyrrolyl

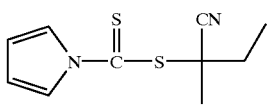

D = D2, R = 2-cyanobut-2-yl
E = E1 = 1-pyrrolyl

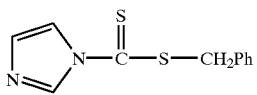

D = D2, R = benzyl; E = E1 = 1-imidazolyl

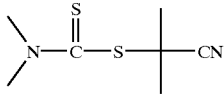

D = D2, R = 2-cyanoprop-2-yl
E = E1, G = J = methyl

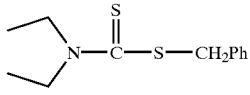

D = D2, R = benzyl
E = E1; G = J = ethyl

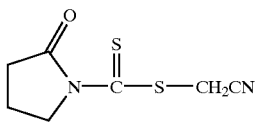

D = D2, R = cyanomethyl;
E = E1 = 1-(pyrrolidin-2-onyl)

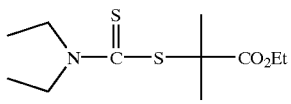

D = D2, R = 2-(ethoxycarbonyl)prop-2-yl;
E = E1; G = J = ethyl (62)

(63)

(64)

(65)

(66)

(67)

(68)

(69)

Procedure 1

Preparation of Benzyl 1-Pyrrolecarbodithioate (60)

Pyrrole (1.34 g, 20 mmol) was added dropwise to a stirred suspension of sodium hydride (0.48 g, 20 mmol) in dimethyl sulfoxide (20 mL). On completion of addition the resulting brown solution was stirred at room temperature for 30 minutes before the addition of carbon disulfide (1.52 g, 20 mmol). The solution was allowed to stir at room temperature for a further half hour and benzyl chloride (2.53 g, 20 mmol) added. Water (20 mL) was added after 1 hour followed by diethyl ether (20 mL). The organic layer was separated and the aqueous layer extracted with diethyl ether (2×20 mL). The combined extracts were dried with magnesium sulfate, filtered and the solvent removed. The crude product was chromatographed using 5% ethyl acetate in petroleum spirits to isolate the product as a yellow oil (2.34 g, 50%). $^1$H-nmr (CDCl$_3$) δ 4.60 (2H), 6.30 (2H), 7.40 (5H), 7.70 (2H). $^{13}$C-nmr (CDCl$_3$) δ 41.7, 114.2, 120.6, 128.0, 128.8, 129.4, 135.0, 189.0.

Example 1

Preparation of Benzyl 1-(2-Pyrrolidinone) carbodithioate (61)

Benzyl chloride (0.8 g, 6.35 mmol) was added to a suspension solution of 1-(2-pyrrolidinone)carbodithioc acid (0.97 g, 6.02 mmol) and potassium carbonate (0.84 g, 6.09 mmol) in absolute ethanol (10 mL) at room temperature. The resulting mixture was stirred at room temperature for three hours. Water (25 mL) was added, then extracted with ethyl acetate (3×20 mL). The combined organic layer was dried over anhydrous sodium sulfate. After removal of solvent, the residue was subjected to column chromatography (Kieselgel-60, 70–230 mesh) using n-hexane initially (to remove unreacted benzyl chloride) and then with ethyl acetate/n-hexane 3:7 as eluent. The title compound, benzyl 1-(2-pyrrolidinone)carbodithioate (61) (1.1 g, 73%) was obtained as a bright yellow solid, m.p. 57–58° C. $^1$H-nmr (CDCl$_3$) δ 2.11 (ddt, 2H), 2.73 (t, 2H), 4.25 (dd, 2H), 4.40 (s, 2H) and 7.20–7.40 (m, 5H).

Example 2

Preparation of Benzyl (1,2-Benzenedicarboximido) carbodithioate (62)

Carbon disulfide (1.0 g, 13.1 mmol) was added slowly over ten minutes to a suspension of potassium phthalimide (1.85 g, 10 mmol) in dimethyl sulfoxide (20 mL) at room temperature. The resulting mixture was allowed to stir for a further five hours at room temperature before the addition of benzyl chloride (1.26 g, 10 mmol). The mixture was then heated at 50° C. for three hours. Water (30 mL) was added, and the mixture extracted with ethyl acetate (3×20 mL). The combined organic layer was dried over anhydrous magnesium sulfate, filtered, and removed on a rotary evaporator to give a yellow oil. The crude reaction mixture was chromatographed (kieselgel-60, 70–230 mesh, ethyl acetate/n-hexane 1:9 as eluent) to give benzyl (1,2-benzenedicarboximido) carbodithioate (62) (180 mg, 5.8% yield). $^1$H-nmr (CDCl$_3$) δ 4.55 (s, 2H), 7.30–7.45 (m, 5H), 7.82 (dd, 2H) and 7.98 (dd, 2H).

Example 3

Preparation of 2-Cyanoprop-2-yl 1-Pyrrolecarbodithioate (63)

Pyrrole N-thiocarbonyl disulfide (0.15 g, 0.53 mmol) and 2,2'-azobis(isobutyronitrile) (0.16 g, 1 mmol) was dissolved in ethyl acetate (5 mL) and transfered into a Young's vessel. The contents were degassed and heated at 70° C. for 24 hours. The solvent was removed under vacuum and the residue chromatographed on silica (10% ethyl acetate/ petroleum spirits) to afford 2-cyanoprop-2-yl 1-pyrrolecarbodithioate (135 mg, 61%). $^1$H-nmr (CDCl$_3$) δ 1.99 (6H), 6.38 (2H), 7.61 (2H). $^{13}$C-nmr (CDCl$_3$) δ 27.0, 114.7, 120.7, 176.4, 193.2.

Example 4

Preparation of 2-Cyanobut-2-yl 1-Pyrrolecarbodithioate (64)

Pyrrole N-thiocarbonyl disulfide (0.71 g, 2.5 mmol) and 2,2'-azobis(2-cyanobutane) (0.63 g, 3.3 mmol) was dissolved in ethyl acetate (10 mL) and transfered into a Young's vessel. The contents were degassed and heated at 70° C. for 24 hours. The solvent was removed under vacuum and the residue chromatographed on alumina (activity III) (15% ethyl acetate/petroleum spirits) to afford 2-cyanobut-2-yl 1-pyrrolecarbodithioate as an oil (310 mg, 28%). The compound gradually decomposes at room temperature and needs to be stored in the freezer. $^1$H-nmr (CDCl$_3$) δ 1.10 (3H, t,), 1.89 (3H, s), 2.22 (2H, m), 6.30 (2H), 7.65 (2H).

Procedure 2

Preparation of Benzyl 1-Imidazolecarbodithioate (65)

Benzyl mercaptan (0.68 g, 5.5 mmol) was added dropwise to a solution of thiocarbonyl diimidazole (0.89 g, 5 mmol) in dichloromethane (10 mL) at room temperature. The solution was allowed to stir for 30 minutes at the same temperature and the solvent was then removed under vacuum. The residue was chromatographed (Kieselgel-60, 70–230 mesh) using ethyl acetate/petroleum spirits 3:7 as eluent to afford benzyl 1-imidazolecarbodithioate (65) (0.78 g, 54%) as a bright yellow solid. $^1$H-nmr (CDCl$_3$) δ 4.60 (2H), 7.10 (1H,), 7.40 (5H,), 7.75 (1H), 8.45 (1H). $^{13}$C-nmr (CDCl$_3$) δ 641.73, 117.6, 131.5, 135.0, 128.3, 128.9, 129.4, 133.8, 188.3.

Example 5

Preparation of N,N-Dimethyl-S-(2-cyanoprop-2-yl) dithiocarbamate (66)

Tetramethylthiuramdisulfide (1.2 g, 5 mmol) and 2,2'-azobis(isobutyronitrile) (1.23 g, 7.5 mmol) was dissolved in benzene. The solution was degassed by bubbling nitrogen through the solution for 10 minutes and heated at reflux for 24 hours. Benzene was removed under reduced presssure and the crude residue chromatographed (silica gel, 30% ethyl acetate in petroleum spirits) to afford the title compound (1.74 g, 93%). $^1$H-nmr (CDCl$_3$) δ 1.9 (6H), 3.4 (6H, bd). $^{13}$C-nmr (CDCl$_3$) δ 27.4, 42.15, 62.5, 122.0, 190.0.

Procedure 3

Preparation of N,N-Diethyl S-Benzyl Dithiocarbamate (67)

Benzyl bromide (2.05 g, 12 mmol) in THF (10 mL) was added dropwise over 15 minutes to a supension of sodium N,N-diethyldithiocarbamate trihydrate (2.25 g, 10 mmol) in 25 mL of THF at room temperature. The solution was allowed to stir at room temperature for 3 hours when the solids were filtered off and the filtrate concentrated. The crude residue was purified by column chromatography (silica gel, 20% ethyl acetate in petroleum spirits) to obtain the title compound (2.25 g, 94%). $^1$H-nmr (CDCl$_3$) δ 1.3 (6H), 3.7 (2H), 4.1 (2H), 4.6 (2H), 7.3 (5H).

Example 6

Preparation of Cyanomethyl 1-(2-Pyrrolidone) carbodithoate (68)

Chloroacetonitrile (1 mL, 15.9 mmol) was added to a suspension solution of 1-(2-pyrrolidinone)carbodithioic acid (0.97 g, 6.02 mmol) and potassium carbonate (0.84 g, 6.09 mmol) in acetonitrile (10 mL) at room temperature. The resulting mixture was stirred at room temperature for 18 hours. Water (25 mL) was added, then extracted with ethyl acetate (3×20 mL). The combined organic layer was dried over anhydrous sodium sulfate. After removal of solvent, the residue was subjected to column chromatography (Kieselgel-60, 70–230 mesh) using ethyl acetate/n-hexane 1:4 as eluent. The title compound, cyanomethyl 1-(2-pyrrolidinone)carbodithioate (0.74 g, 65.5% yield) was obtained as a yellow solid, m.p. 65–66° C. $^1$H-nmr (CDCl$_3$) δ 2.20 (ddt, 2H), 2.80 (t, 2H), 4.00 (s, 2H) and 4.25 (dd, 2H).

Procedure 4

Preparation of N,N-Diethyl S-(2-Ethoxycarbonylprop-2-yl)dithiocarbamate (69)

The title compound was prepared according to T. Otsu, T. Matsunaga, T. Doi and A. Matsumoto, *Eur. Polym. J.* 31, 67–78 (1995).

Examples 6–11 illustrate the synthesis of thiocarbonylthio compounds with an α-oxygen substituent (xanthate esters formula 2 D=D2, E=E2)

(70)

D = D2, R = 1-phenylethyl
E = E2, G' = ethyl

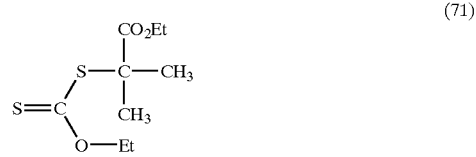

(71)

D = D2, R = 2-(ethoxycarbonyl)prop-2-yl
E = E2; G' = ethyl

(72)

D = D2, R = 2-cyanoprop-2-yl
E = E2; G' = ethyl

(73)

D = D2, R = cyanomethyl
E = E2, G' = ethyl

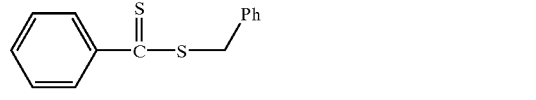

(74)

D = D2, R = benzyl
E = E2; G' = phenyl

-continued

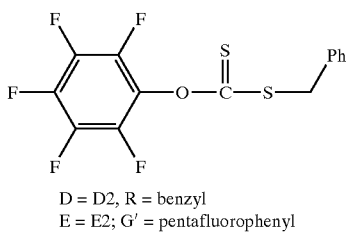

D = D2, R = benzyl
E = E2; G' = pentafluorophenyl (75)

Procedure 5

Preparation of O-Ethyl S-(1-Phenylethyl)xanthtate (70)

A solution of 1-(bromoethyl)benzene (3.7 g) and potassium O-ethyl dithiocarbonate (3.2 g) in ethanol (50 mL) was stirred at room temperature for 16 hours. The reaction was diluted with water (50 mL) and the organics extracted with n-hexane. The combined organic layers were washed with water, brine and dried over magnesium sulfate. The solvent was evaporated and the title compound was obtained as a yellow oil (4.4 g, 97%).

Example 7

Preparation of O-Ethyl S-(2-(Ethoxycarbonyl)prop-2-yl)xanthate (71)

A solution of 2-bromoisobutyrate (19.5 g) and potassium O-ethyl dithiocarbonate (16.0 g) in ethanol (200 mL) were allowed to stir at room temperature for 20 hours and then at 50° C. for 16 hours. The reaction was diluted with water (200 mL) and the organics extracted with n-hexane. The combined organic layers were washed with water, brine and dried over anhydrous sodium sulfate. The solvent was evaporated and the residue purified by column chromatography (Alumina oxide 90 70–230 mesh, Activity II–III) eluting with 1:9 diethyl ether:n-hexane to afford the title compound as a yellow oil (40% yield).

Example 8

Preparation of O-Ethyl S-(2-Cyanoprop-2-yl) xanthate (72) from Potassium O-Ethyl Dithiocarbonate A solution of bromoisobutyronitrile (10 g) and potassium O-ethyl dithiocarbonate (10.84 g) in ethanol (280 g) were heated at 40° C. with stirring for 40 hours. The mixture was then allowed to stir for 12 days at room temperature. The reaction mixture was diluted with water (400 mL) and the organics extracted with n-hexane. The combined organic layers were washed with water, brine and dried over magnesium sulfate. The solvent was evaporated and the residue purified by column chromatography (Alumina oxide 90 70–230 mesh, Activity II–III) eluting with a gradient of 1:9 diethyl ether: hexane to 1:4 diethyl ether.

Example 9

Preparation of O-Ethyl S-(2-Cyanoprop-2-yl) xanthate (72) from O-Ethyl Xanthogen Disulfide O-ethyl xanthogen disulfide was prepared by oxidizing an aqueous solution of potassium O-ethyl dithiocarbonate with $I_2$/KI (10%) solution.

A solution of O-ethyl xanthogen disulfide (2.16 g, 8.92 mmol) and 2,2'-azobis(isobutyronitrile) (2.19 g, 13.35 mmol) in ethyl acetate (30 mL) was prepared. The mixture was heated at reflux for 16 hours. The volatiles were removed under reduced pressure and the residue chromatographed using a mixture of ethyl acetate:petroleum spirits (3:47) as eluent to isolate the title compound (3.17 g, 94%). $^1$H-nmr (CDCl$_3$) δ 1.52 (t, 3H); 1.75 (s, 6H) and 4.75 (q, 2H). $^{13}$C-nmr (CDCl$_3$) δ 13.4; 27.2; 40.8; 70.6; 121.1 and 208.2.

Example 10

Preparation of O-Ethyl S-Cyanomethyl Xanthate (73)

A solution of bromoacetonitrile (12.4 g) and potassium O-ethyl dithiocarbonate (16.0 g) in ethanol (200 mL) were allowed to stir at room temperature for 16 hours. The reaction was diluted with water (100 mL) and the organics extracted with diethyl ether. The combined organic layers were washed twice with water, then brine and dried over anhydrous magnesium sulfate. The solvent was evaporated and the residue purified by column chromatography (silicagel 60, 70–230 mesh) eluting with 4:6 ethyl acetate: petroleum spirit 40–60° C. to afford the title compound as a yellow oil (14.6 g, 90.7%). $^1$H-nmr (CDCl$_3$) δ 1.48 (t, 3H); 3.88 (s, 2H); 4.72 (q, 2H). $^{13}$C-nmr (CDCl$_3$) δ 13.7, 21.3, 71.5, 115.7, 209.2.

Example 11

Preparation of O-Phenyl S-Benzyl Xanthate (74)

Benzyl mercaptan (1.24 g, 10 mmol) was added to an aqueous (20 mL) solution of NaOH (0.8 g, 20 mmol) at room temperature and stirred for 15 minutes. Phenyl thionochloroformate (2.07 g, 12 mmol) was next added dropwise to this solution at the same temperature and stirred for a further 2 hours. Diethyl ether (20 mL) and water (50 mL) was added and the organic layer separated. The aqueous layer was extracted with diethyl ether (3×20 mL). The combined organic fractions were dried with Na$_2$SO$_4$, filtered, the solvent removed and the crude product chromatographed (using silica gel, 2% ethyl acetate in petroleum spirits) to afford the title compound (1.95 g, 75%) as a yellow oil. $^1$H-nmr (CDCl$_3$) δ 4.43 (2H), 7.10–7.50 (10H). $^{13}$C-nmr (CDCl$_3$) δ 41.7, 122.1, 126.7, 127.8, 128.8, 129.3, 129.6, 135.1, 154.0, 213.0.

Example 12

Preparation of O-Pentafluorophenyl S-Benzyl Xanthate (75)

Thiophosgene (1.93 g, 16.6 mmol) in CHCl$_3$ (10 mL) at 0° C. was treated dropwise with pentafluorophenol in 5% NaOH (15 mL) cooled to 0–10° C. The solution was stirred for 1 hour at the same temperature, the CHCl$_3$ layer separated and washed with 5% NaOH (10 mL), 5% HCl (10 mL) and H$_2$O 10 mL). The organic portions were combined, dried with MgSO$_4$, filtered and the solvent removed to obtain the perfluorophenyl chloroformate (3.76 g).

Benzyl mercaptan (1.24 g, 10 mmol) was added to 0.8 g of NaOH dissolved in 20 mL of H$_2$O and allowed to stir for 10 minutes. The crude chloroformate (2.63 g, 10 mmol) was added to the solution and stirred for 2 hours. The aqueous solution was extracted with diethyl ether (3×30 mL), organic portions combined, dried with Na$_2$SO$_4$ filtered and the solvent removed. The residue was chromatographed with 2% ethylacetate in petroleum spirits to afford the product (890 mg, 25%). $^1$H-nmr (CDCl$_3$) δ 4.5 (2H), 7.3 (5H). $^{13}$C-nmr (CDCl$_3$) δ 42.9, 128.2, 128.9, 129.2, 134.0. $^{19}$F-nmr (CDCl$_3$) δ −162.54 (2F, t), −156.94 (1F, t), −151.51 (2F, d).

Examples 13 and 14 illustrate the synthesis of vinylogous dithiocompounds (formula 2 D=D1)

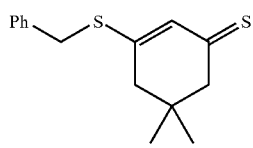
(30)

D = D1, R = benzyl
X = methine
Z', E = neopentylene

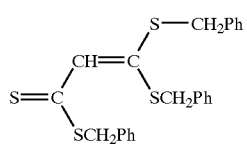
(76)

D = D1, R = benzyl
X = methine
Z' = benzylthio
E, Z' = benzylthio

Example 13

Preparation of 3-Benzylthio-5,5-dimethylcyclohex-2-ene-1-thione (30)

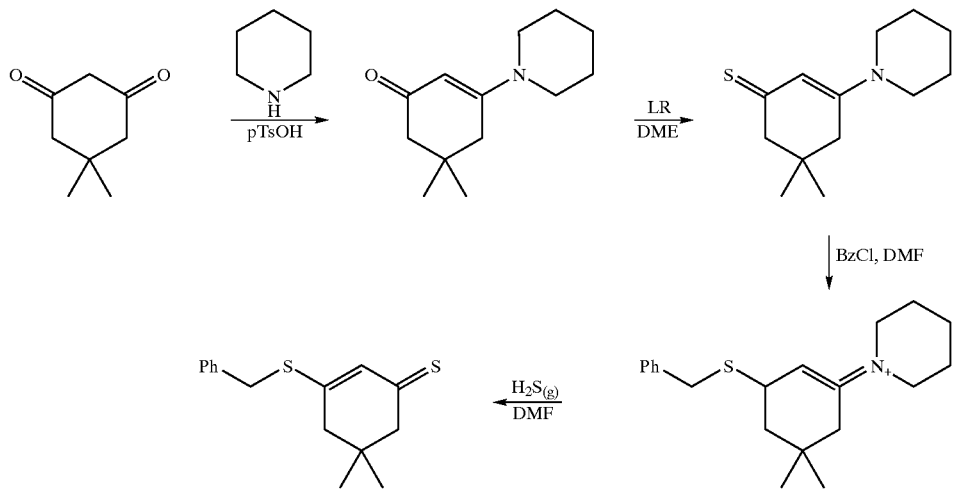

5,5-Dimethyl-3-piperidinyl-cyclohex-2-en-1-one. Piperidine (7.0 mL; 0.0713 mol) and a catalytic quantity of p-toluenesulfonic acid monohydrate was added to a solution of 5,5-dimethylcyclohexane-1,3-dione (110.0 g; 0.0713 mol) in benzene (100 mL) and the resultant solution was heated at reflux. After 3 hours further piperidine (0.71 mL; 7.13 mmol) was added and the solution was allowed to reflux for a further 16 hours. The reaction mixture was cooled to room temperature and washed with 10% NaHCO$_3$ solution (20 mL), dried over anhydrous sodium sulfate and the solvent evaporated (in vacuo) to leave an orange crystalline solid. (14.23 g, 96%). $^1$H-nmr (CDCl$_3$) d: 5.3, (s 1H, H-2), 3.4–3.2 (m, 4H, H-2', H-6'), 2.2 (s, 2H, H-6), 2.1 (s, 2H, H-4), 1.75–1.4 (m, 6H, H-3', H-4', H-5'), 1.00 (s, 6H, 2×CH$_3$).

5,5-Dimethyl-3-piperidinyl-cyclohex-2-ene-1-thione. The compound was prepared according to the procedure of Walter, W. and Proll [Walter, W. and Proll, T., *Synthesis*, 941–2 (1979)]. To a solution of the above enamine (1.0 g; 4.82 mmol) in anhydrous DME 10 mL), was added Lawesson's reagent (1.04 g; 2.57 mmol) over 20 min. at room temperature and under argon. The resulting suspension was stirred at room temperature for 2 hours. The mixture was added to ice water 10 mL) and extracted with CH$_2$Cl$_2$ (3×20 mL). The combined extracts were dried over anhydrous sodium sulfate and the solvent evaporated in vacuo to leave an orange solid. The crude solid was chromatographed on a mixture of silica gel and basic alumina (1:1) using chloroform as eluent. The title compound was obtained as an orange solid (1.1 g, 100%). $^1$H-nmr (CDCl$_3$) d: 6.75 (s, 1H, H-2), 3.6–3.4 (m, 4H, H-2', H-6'), 2.65 (s, 2H, H-6) 2.2 (s, 2H, H-4), 1.75–1.5 (m, 6H, H-3', H-4', H-5'), 1.00 (s, 6H, 2×CH$_3$).

3-Benzylthio-5,5-dimethylcyclohex-2-ene-1-thione. The compound was prepared according to the procedure of Timokhina et al [Timokhina, L. V. et al, *Zh. Org. Khim.*, 14, 2226–7 (1978)]. To a cold (0° C.) solution of the above enaminothione (0.50 g, 2.24 mmol) in anhydrous DMF (5 mL), was added benzyl chloride (0.35 g, 2.7 mmol) over 30 min. under Argon. The mixture was allowed to warm to room temperature and stirred for a further 2 hours. The mixture was cooled to −50° C. (dry ice/benzyl acetate) and anhydrous H$_2$S (g) was passed through the solution for 2 hours. The red solution was poured into ice water (10 mL) and extracted with CH$_2$Cl$_2$ (2×20 mL). The combined extracts were dried over anhydrous sodium sulfate and the solvent removed in vacuo to give a purple oil (0.52 g. 89%). $^1$H-nmr (CDCl$_3$) d: 7.4–7.1 (m, 5H, ArH) 6.9 (s, 1H, H-2), 4.15 (s, 2H, SCH$_2$Ph) 2.8 (s, 2H, H-6), 2.25 (s, 2H, H-4) 1.00 (s, 6H, 2×CH$_3$).

Example 14

Preparation of Benzyl 3,3-di(Benzylthio)prop-2-enedithioate (76)

Carbon disulfide (0.76 g, 10 mmol) was added dropwise to methyl magnesium chloride (1.67 mL, 5 mmol, 3M solution in diethyl ether) in THF (3.5 mL) at room temperature. After 2 hours, the solution was cooled to −78° C. (dry ice/acetone) and lithium di-isopropylamide (10 mmol, 6.67 mL of 1.5 M solution in hexane) was added over 30 minutes. The solution was stirred at −78° C. for 45 minutes, then at room temperature for a further 30 minutes before benzyl bromide (1.89 g, 15 mmol) was added. The solution was warmed to 40° C. for 2 hours and stirred overnight at room temperature. A 5% solution of $NaHCO_3$ (30 mL), followed by 20 mL of diethyl ether was added to the mixture and the organic layer separated. The aqueous layer was extracted with diethyl ether (3×20 mL), the organic layers combined, dried over $MgSO_4$, filtered and the solvent evaporated. The residue was chromatographed on silica gel (5% ethyl acetate in petroleum spirits) to afford the product (0.63 g, 29% yield) as an orange solid. $^1$H-nmr ($CDCl_3$) δ 4.19, 4.30, 4.42 (6H, s, $CH_2Ph$), 7.05 (1H, CH), 7.35 (15H, ArH). $^{13}$C-nmr ($CDCl_3$) δ 37.6, 39.6, 39.9, 124.4 (CH), 124.4, 127.4, 127.7, 128.2, 128.5, 128.7, 129.0, 129.2, 129.3, 133.8, 135.4, 136.2. 159.1, 209.4. m/z: AP+ 439 (M+1), AP− 438 (M−1).

The following examples demonstrate the application of the dithio-compounds with an α-nitrogen substituent which is an electron withdrawing/conjugating group to the synthesis of narrow polydispersity polymers.

Examples 15–19

Styrene Polymerizations in the Presence of α-Nitrogen Dithio-compounds

Thermal polymerizations of styrene were carried out in the presence of benzyl 1-pyrrolecarbodithioate (60), benzyl 1-(2-pyrrolidinone)carbodithioate (61), and benzyl (1,2-benzenedicarboximido)carbodithioate (62).

Freshly distilled styrene (1 mL) was added to six separate ampoules containing the required amount of dithiocarbamate (see Table 1). The contents of ampoules were degassed, sealed and heated at 110° C. for 16 hours. After removal of the volatiles, the residue was analyzed by GPC.

TABLE 1

Molecular weight and conversion data for polystyrene prepared in the presence of dithiocarbamates (60–62) at 110° C.

| Example | Dithio compound | Dithio (mg) | $M_n$ | $M_w/M_n$ | % Conv. |
|---|---|---|---|---|---|
| 15 | (60) | 6.92 | 30674 | 1.18 | 58 |
| 16 | (60) | 13.75 | 16018 | 1.18 | 59 |
| 17 | (61) | 7.42 | 40515 | 1.63 | 57 |
| 18 | (61) | 14.82 | 22510 | 1.58 | 57 |
| 19 | (62) | 9.07 | 23480 | 1.10 | 51 |

Example 20

Methyl Acrylate Polymerization in the Presence of a Low Concentration of Benzyl 1-Pyrrolecarbodithioate (60)

A stock solution of the dithiocarbamate (60) (8.6 mg), 2,2'-azobis(isobutyronitrile) (3.0 mg) and methyl acrylate (5 mL) in benzene (20 mL) was prepared. Three 5 mL aliquots of this solution were transferred to ampoules which were degassed, sealed and heated at 60° C. for 1, 8 and 16 hours respectively. The resulting polymers were analyzed by GPC after the removal of excess monomer and solvent.

TABLE 2

Molecular weight and conversion data for polymerization of methyl acrylate in the presence of benzyl 1-pyrrolecarbodithioate (60) (8.6 mg) with 2,2'-azobis(isobutyronitrile) as initiator at 60° C.

| Entry | Time/hr | $M_n$ | $M_w/M_n$ | % Conv. |
|---|---|---|---|---|
| 1 | 1 | 37257 | 1.18 | 31 |
| 2 | 8 | 97127 | 1.37 | 89 |
| 3 | 16 | 110906 | 1.36 | 91 |

Example 21

Methyl Acrylate Polymerization in the Presence of a High Concentration of Benzyl 1-Pyrrolecarbodithioate (60)

A solution of the dithiocarbamate (60) (86.0 mg), 2,2'-azobis(isobutyronitrile) (3.0 mg) and methyl acrylate (5 mL) in benzene (20 mL) was prepared. Three 5 mL aliquots of this solution were transferred to ampoules, degassed, sealed and heated at 60° C. for 4, 8 and 16 hours respectively. The resulting polymers were analysed by GPC after the removal of excess monomer and solvent

TABLE 3

Molecular weight and conversion data for polymerization of methyl acrylate in the presence of benzyl 1-pyrrolecarbodithioate (60) (86.0 mg) with 2,2'-azobis(isobutyronitrile) as initiator at 60° C.

| Entry | Time/hr | $M_n$ | $M_w/M_n$ | % Conv. |
|---|---|---|---|---|
| 1 | 4 | 3381 | 1.36 | 22 |
| 2 | 8 | 5952 | 1.22 | 47 |
| 3 | 16 | 8762 | 1.17 | 74 |

The presence of the end groups (pyrrole and benzyl) was confirmed by $^1$H NMR.

Examples 22, 23

Methyl Acrylate Polymerization in the Presence of Benzyl 1-(2-Pyrrolidinone)carbodithioate (61) and Benzyl (1,2-Benzenedicarboximido)carbodithioate (62)

A stock solution comprising of 2,2'-azobis(isobutyronitrile) (2.30 mg) in benzene (25 mL) was prepared. Aliquots (6.0 mL) were transferred into two separate ampoules already containing methyl acrylate (4.0 mL) and the dithiocarbamate [4.63 mg for (61); 5.20 mg for (62)]. The contents of both ampoules were degassed, sealed and heated at 60° C. for 16 hours.The results are listed in Table 4.

TABLE 4

Molecular weight and conversion data for poly(methyl acrylate) prepared in the presence of (61) and (62) at 60° C.

| Example | Dithioester | Dithio (mg) | $M_n$ | $M_w/M_n$ | % Conv. |
|---|---|---|---|---|---|
| 22 | (61) | 4.63 | 161800 | 1.21 | 89 |
| 23 | (62) | 5.20 | 59800 | 1.52$^a$ | 48 |

$^a$Bimodal molecular weight distribution.

Example 24

Methyl Acrylate Polymerization in the Presence of 2-Cyanoprop-2-yl 1-Pyrrolecarbodithioate (63)

A solution of the dithiocarbamate (63) (8.95 mg), 2,2'-azobis(isobutyronitrile) (3.1 mg) and methyl acrylate (5 mL)

in benzene (20 mL) was prepared. Three 5 mL aliquots of this solution were transferred to ampoules, degassed, sealed and heated at 60° C. for 1, 4 and 16 hours respectively. The resulting polymers were analysed by GPC after the removal of excess monomer and solvent.

TABLE 5

Molecular weight and conversion data for polymerization of methyl acrylate in the presence of 2-cyanoprop-2-yl 1-pyrrolecarbodithioate (63) with 2,2'-azobis(isobutyronitrile) as initiator at 60° C.

| Entry | Time/hr | $M_n$ | $M_w/M_n$ | % Conv. |
|---|---|---|---|---|
| 1 | 1 | 30308 | 1.11 | 20 |
| 2 | 4 | 82255 | 1.13 | 56 |
| 3 | 16 | 131558 | 1.40 | 91 |

Example 25

Methyl Acrylate Polymerization in the Presence of Benzyl 1-Imidazole Carbodithioate (65)

A solution of the dithiocarbamate (65) (8.6 mg), 2,2'-azobis(isobutyronitrile) (2.7 mg) and methyl acrylate (5 mL) in benzene (20 mL) was prepared. Three 5 mL aliquots of this solution were transferred to ampoules, degassed, sealed and heated at 60° C. for 1, 4 and 16 hours respectively. The resulting polymers were analysed by GPC after the removal of excess monomer and solvent.

TABLE 6

Molecular weight and conversion data for polymerization of methyl acrylate in the presence of benzyl 1-imidazole carbodithioate (65) (8.6 mg) using 2,2'-azobis(isobutyronitrile) as initiator at 60° C.

| Entry | Time/hr | $M_n$ | $M_w/M_n$ | % Conv. |
|---|---|---|---|---|
| 1 | 1 | 22189 | 1.13 | 16 |
| 2 | 4 | 82574 | 1.14 | 66 |
| 3 | 16 | 107077 | 1.34 | 97 |

Example 26

Methyl Methacrylate Polymerization in the Presence of 2-Cyanoprop-2-yl 1-Pyrrolecarbodithioate (63)

A solution of the dithiocarbamate (63) (10.4 mg), 2,2'-azobis(isobutyronitrile) (10.1 mg) and methyl methacrylate (7.55 mL) in benzene (2.5 mL) was prepared. Four 2 mL aliquots of this solution were transferred to ampoules, degassed, sealed and heated at 60° C. for 1, 4, 8 and 16 hours respectively. The resulting polymers were analysed by GPC after the removal of excess monomer and solvent.

TABLE 7

Molecular weight and conversion data for polymerization of methyl methacrylate with 2-cyanoprop-2-yl 1-pyrrolecarbodithioate (63) using 2,2'-azobis(isobutyronitrile) as initiator at 60° C.

| Entry | Time/hr | $M_n$ | $M_w/M_n$ | % Conv. |
|---|---|---|---|---|
| 1 | 1 | 42450 | 1.70 | 16 |
| 2 | 4 | 64025 | 1.50 | 51 |
| 3 | 8 | 114561 | 1.26 | >95 |
| 4 | 16 | 117418 | 1.27 | >95 |

Example 27

Methyl Methacrylate Polymerization in the Presence of 2-Cyanobut-2-yl 1-Pyrrolecarbodithioate (64)

A solution of the CTA (64) (24.97 mg), 2,2'-azobis(2-cyanobutane) (11.7 mg) and methyl methacrylate (7.5 mL) in benzene (2.5 mL) was prepared. Four 2 mL aliquots of this solution were transferred to ampoules, degassed, sealed and heated at 60° C. for 2, 4, 8 and 16 hours respectively. The resulting polymers were analysed by GPC after the removal of excess monomer and solvent.

TABLE 8

Molecular weight and conversion data for polymerization of methyl methacrylate in the presence of 2-cyanobut-2-yl 1-pyrrolecarbodithioate (64) with 2,2'-azobis(2-cyanobutane) as initiator at 60° C.

| Entry | Time/hr | $M_n$ | $M_w/M_n$ | % Conv. |
|---|---|---|---|---|
| 1 | 2 | 19372 | 1.58 | 21 |
| 2 | 4 | 28752 | 1.44 | 52 |
| 3 | 8 | 35888 | 1.30 | 65 |
| 4 | 16 | 57378 | 1.21 | 99 |

The following example illustrates the effectiveness of a dithiocarbamate with an α-nitrogen substituent which is a capable of delocalising the nitrogen lone pair in controlling polydispersity of poly(methyl methacrylate). A control experiment carried out with N,N-dimethyl-S-(2-cyanoprop-2-yl) dithiocarbamate (66) shows that dithiocarbamates with simple alkyl substituents are not effective in controlling molecular weight or polydispersity.

Example 28

Methyl Methacrylate Polymerization in the Presence of 2-Cyanoprop-2-yl-1-Pyrrolecarbodithioate (63) or N,N-Dimethyl-S-(2-cyanoprop-2-yl) Dithiocarbamate (66)

Stock solutions, I comprising 2,2'-azobis(isobutyronitrile) (24.09 mg) in 5 mL of benzene, II comprising N,N-dimethyl-S-(2-cyanoprop-2-yl) dithiocarbamate (66) (5.61 mg) in 2 mL of MMA and III comprising 2-cyanoprop-2-yl-1-pyrrolecarbodithioate (63) (15.67 mg) in 5 mL of MMA were prepared. Four 0.5 mL aliquots of stock solution I were transferred to four ampoules. An aliquot of 1.5 mL of stock solution II was transferred to one of the above ampoules which was degassed, sealed and heated at 60° C. for 8 hours. Three 1.5 mL aliquots of stock solution m were transferred to the three remaining ampoules which were degassed, sealed and heated at 60° C. for 2, 8, 16 hours. The respective polymers were analysed by GPC after removal of excess monomer.

TABLE 9

Molecular weight and conversion data for poly(methyl methacrylate) prepared in the presence of dithiocarbamate derivatives at 60° C.

| Entry | Dithio compound | Time/hr | $M_n$ | $M_w/M_n$ | % Conv. |
|---|---|---|---|---|---|
| 1 | (66) | 8 | 312 462 | 1.94 | >95 |
| 2 | (63) | 2 | 22 758 | 1.54 | 33.2 |
| 3 | (63) | 8 | 48 257 | 1.25 | 92.3 |
| 4 | (63) | 16 | 51 474 | 1.19 | >95 |

The following example illustrates the effectiveness of a dithiocarbamate with an α-nitrogen substituent which is a capable of delocalizing the nitrogen lone pair in controlling polydispersity of polystyrene. A control experiment carried out with N,N-diethyl S-benzyl dithiocarbamate (67) shows that dithiocarbamates with simple alkyl substituents are not effective in controlling molecular weight or polydispersity.

Example 29

Styrene Polymerization Using Benzyl-1-pyrrolecarbodithioate (60) and N,N-Diethyl S-Benzyl Dithiocarbamate (67)

Solutions I of benzyl-1-pyrrolecarbodithioate (60) (55.4 mg) in 8 mL of styrene and II of N,N-diethyl S-benzyl dithiocarbamate (67) (14.2 mg) in 2 mL of styrene were prepared. 2 mL aliquots of the solution I were transferred to each of three ampoules which were degassed, sealed and heated at 100° C. for 1, 6 and 30 hours. Solution II was placed in an ampoule, degassed, sealed and heated at 100° C. for 6 hours. The respective polymers were analyzed by GPC after removal of excess monomer.

TABLE 10

Molecular weight and conversion data for polystyrene prepared in the presence of dithiocompounds (60 & 67) at 100° C.

| Entry | Xanthates | Time/hr | $M_n$ | $M_w/M_n$ | % Conv. |
|---|---|---|---|---|---|
| 5 | (67) | 6 | 317 114 | 1.86 | 15.3 |
| 6 | (60) | 1 | 3 844 | 1.63 | 2.9 |
| 7 | (60) | 6 | 6 478 | 1.46 | 10.2 |
| 8 | (60) | 30 | 15 605 | 1.20 | 59.6 |

The following example shows that dithiocarbamates with simple alkyl substituents are effective in controlling molecular weight and polydispersity of poly(vinyl acetate).

Example 30

Preparation of narrow polydispersity poly(vinyl acetate) in the presence of N,N-diethyl S-(2-ethoxycarbonylprop-2-yl) dithiocarbamate (69)

A stock solution comprising of 1,1'-azobis(cyclohexanecarbonitrile) (2.26 mg), vinyl acetate (10 mL) and N,N-diethyl S-(2-ethoxycarbonylprop-2-yl) dithiocarbamate (69) (231.53 mg) was prepared. Aliquots (2 mL) of this stock solution were then transferred to ampoules. The contents of ampoules were degassed, sealed and heated at 100° C. for specified time. Results are summarized in Table 11.

TABLE 11

Molecular weight and conversion data for poly(vinyl acetate) in the presence of N,N-diethyl S-(2-ethoxycarbonylprop-2-yl) dithiocarbamate (69) at 100° C.

| Entry | Reaction time (hr) | $M_n$ | $M_w/M_n$ | % Conversion |
|---|---|---|---|---|
| 1 | 1 | 4500 | 1.64 | 8.4 |
| 2 | 2 | 6150 | 1.61 | 32.4 |
| 3 | 4 | 9500 | 1.47 | 68.0 |
| 4 | 16 | 10550 | 1.43 | 76.5 |

The following examples relate to the measurement of transfer constants of xanthate derivatives in polymerizations of n-butyl acrylate (example 31), t-butyl acrylate (examples 32, 33) and methyl methacrylate (examples 34). The magnitude of the transfer constants show that it should be possible to achieve narrow polydispersities (<1.5) in feed polymerization processes in polymerizations of acrylate esters.

Example 31

Preparation of Poly(n-butyl Acrylate) in the Presence of O-Ethyl S-(1-Phenylethyl)xanthate (70)

A stock solution comprising of 2,2'-azobis (isobutyronitrile) (13.4 mg) in benzene (50 mL) was prepared. Aliquots (2 mL) of this stock solution were then transferred to four separate ampoules containing n-butyl acrylate (4 mL), benzene (4 mL) and O-ethyl S-(1-phenylethyl)xanthate. The contents of ampoules were degassed, sealed and heated at 60° C. for one hour. The results are summarized in the following Table.

TABLE 12

Molecular weight and conversion data for poly(n-butyl acrylate) in the presence of O-ethyl S-(1-phenylethyl) xanthate (70) at 60° C.

| Entry | [CTA]/[MMA] | $M_n$ | $M_w/M_n$ | % Conversion |
|---|---|---|---|---|
| 1 | 0 | 1027396 | 1.78 | 29 |
| 2 | 0.00081 | 70196 | 1.85 | 11 |
| 3 | 0.00166 | 40555 | 1.77 | 16 |
| 4 | 0.00325 | 19411 | 1.87 | 12 |

Analysis of the data via a Mayo plot shows that the transfer constant of O-ethyl S-(1-phenylethyl)xanthate in n-butyl acrylate polymerization is 2.0.

Example 32

Preparation of Poly(t-butyl Acrylate) in the Presence of O-Pentafluorophenyl S-Benzyl Xanthate (75)

Aliquots (2 mL) of a solution of 2,2'-azobis (isobutyronitrile) (13.4 mg) in benzene (43.7 g, 50 mL) were added to each of four ampoules containing t-butyl acrylate (4 mL), benzene (4 mL) and the required amount of O-pentafluorophenyl S-benzyl xanthate (75). The ampoules were degassed, sealed and heated at 60° C. for 60 minutes. Results are summarized in the following Table.

TABLE 13

Molecular weight and conversion data for poly(t-butyl acrylate) in the presence of O-pentafluorophenyl S-benzyl xanthate (75) at 60° C$^a$.

| Entry | [CTA] (mol/L) | [CTA]/[M] | $M_n$ | $M_w/M_n$ | Conv. (%) |
|---|---|---|---|---|---|
| 1 | 0 | 0 | 1467774 | 1.68 | 45.1 |
| 2 | 2.886e-3 | 1.057e-3 | 42024 | 1.83 | 26.5 |
| 3 | 5.247e-3 | 1.922e-3 | 22214 | 1.83 | 24.1 |
| 4 | 1.140e-2 | 4.176e-3 | 10850 | 1.76 | 16.0 |

$^a$[AIBN] = 3.273e-4 M, [t-butyl acrylate] = 2.73 M at 25° C.

Analysis of the data via a Mayo plot shows that the transfer constant of O-pentafluorophenyl S-benzyl xanthate in t-butyl acrylate polymerization is 2.7.

Example 33

Preparation of Poly(t-butyl Acrylate) in the Presence of O-Ethyl S-(2-Cyanoprop-2-yl)xanthate (72)

Aliquots (2 mL) of a solution of 2,2'-azobis (isobutyronitrile) (13.5 mg) in benzene (43.6 g, 50 mL) were added to each of four ampoules containing t-butyl acrylate (4 mL), benzene (4 ml) and the required amount of O-ethyl S-(2-cyanoprop-2-yl)xanthate (72). The ampoules were degassed, sealed and heated at 60° C. for 60 minutes. Results are summarized in the following Table.

TABLE 14

Molecular weight and conversion data for poly(t-butyl acrylate) in the presence of O-ethyl S-(2-cyanoprop-2-yl) xanthate (72) at 60° C[a].

| Entry | [CTA] (mol/L) | [CTA]/[M] | $M_n$ | $M_w/M_n$ | Conv. (%) |
|---|---|---|---|---|---|
| 1 | 0 | 0 | 1790182 | 1.52 | 38.9 |
| 2 | 2.916e-3 | 1.068e-3 | 18775 | 1.81 | 7.68 |
| 3 | 5.320e-3 | 1.948e-3 | 9438 | 1.81 | 5.13 |
| 4 | 1.053e-2 | 3.856e-3 | 4611 | 1.80 | 4.26 |

[a][AIBN] = 3.283e-4 M, [t-butyl acrylate] = 2.73 M at 25° C.

Analysis of the data via a Mayo plot shows that the transfer constant of O-ethyl S-(2-cyanoprop-2-yl)xanthate in t-butyl acrylate polymerization is 7.25.

Example 34

Preparation of Poly(methyl Methacrylate) in the Presence of O-Ethyl S-(2-Cyanoprop-2-yl)xanthate (72)

Aliquots (5 mL) of a solution of azobis(isobutyronitrile) (50.3 mg) in methyl methacrylate (23.4 g, 25 mL) were added to each of four ampoules containing the required amount of O-ethyl S-(2-cyanoprop-2-yl)xanthate (72). The ampoules were degassed, sealed and heated at 60° C. for 60 minutes. Results are summarized in the following Table.

TABLE 15

Molecular weight and conversion date for poly(methyl methacrylate) prepared in the presence of O-ethyl S-(2-cyanoprop-2-yl) xanthate (72).

| Entry | [CTA]/[MMA] | $M_n$ | $M_w/M_n$ | % Conversion |
|---|---|---|---|---|
| 1 | 0 | 316205 | 2.20 | 13.6 |
| 2 | 0.00073 | 278090 | 2.13 | 13.9 |
| 3 | 0.00176 | 255183 | 1.94 | 13.8 |
| 4 | 0.00303 | 233881 | 1.83 | 15.3 |

[a][AIBN] = 1.225e-2 M, [methyl methacrylate] = 9.35 M at 25° C.

Analysis of the data via a Mayo plot shows that the transfer constant of O-ethyl S-(2-cyanoprop-2-yl)xanthate in methyl methacrylate polymerization is ca. 0.04.

The following example shows that it is possible to use xanthate esters to control the molecular weight and polydispersity of polymer formed in miniemulsion polymerization.

Example 35

Preparation of Polystyrene via Miniemulsion Polymerization with O-Ethyl S-(1-Phenylethyl) xanthate (70) at 70° C.

A 5-neck reaction vessel fitted with a stirrer, condenser and thermocouple was charged with water (75 g) and sodium dodecyl sulfate (215.2 mg), cetyl alcohol (53 mg), sodium bicarbonate (16.7 mg). The mixture was then homogenized for 10 minutes. Styrene (18.84 g) was added and the mixture homogenized for a further 5 minutes. The reaction mixture was stirred (300 rpm) for 40 minutes while the temperature was raised to 70° C. O-ethyl S-(1-phenylethyl)xanthate (87 mg) and 2,2'-azobis(2-cyano-2-butane) (40.7 mg) were then added.

TABLE 16

Molecular weight and conversion data for polystyrene prepared with O-ethyl S-(1-phenylethyl) xanthate (70) by mini-emulsion polymerization at 70° C.

| Example | Reaction time /min | $M_n$ | $M_w/M_n$ | % Conversion |
|---|---|---|---|---|
| control[a] | 60 | 930564 | 6.98 | 13 |
| Ex 35 | 60 | 84740 | 1.4 | 11 |

[a]no xanthate

The following examples show that it is possible to use xanthate esters to control the molecular weight and polydispersity of vinyl ester polymers (e.g. vinyl benzoate, vinyl acetate).

Example 36

Preparation of Poly(vinyl Benzoate) in the Presence of O-Ethyl S-(2-Cyanoprop-2-yl)xanthate (72) at 150° C.

A solution of azobis(isobutyronitrile) (0.14 mL of 1% solotion in vinyl benzoate) and O-ethyl S-(2-cyanoprop-2-yl)xanthate (72) (43.5 mg) in vinyl benzoate (3 g) was transferred to an ampoule which was degassed, sealed and heated at 150° C. for 24 hours. A control prepared similarly contained no xanthate. Results are summarized in the following Table.

TABLE 17

Molecular weight and conversion data for poly(vinyl benzoate) in the presence of O-ethyl S-(2-cyanoprop-2-yl) xanthate (72) at 150° C.

| Example | Reaction time (hr) | $M_n$ | $M_w/M_n$ | % Conversion |
|---|---|---|---|---|
| control[a] | 24 | 381980 | 2.07 | 88 |
| Ex 35 | 24 | 9140 | 1.43 | 12 |

[a]no xanthate

Example 37

Preparation of Narrow Polydispersity Poly(vinyl Acetate) in the Presence of O-Ethyl S-Cyanomethyl Xanthate (73)

A stock solution (1) of 1,1'-azobis(cyclohexanecarbonitrile) (2.11 mg), vinyl acetate (25 mL) in ethyl acetate (25 mL) was prepared. Aliquot (10 mL) of solution (I) was transferred to a 10 mL volumetric flask already containing O-ethyl S-cyanomethyl xanthate (73) (20.18 mg) for the preparation of stock solution (II). Aliquots (2 mL) of the stock solution (II) were transferred to ampoules. The ampoules were degassed, sealed and heated at 100° C. for specified time. Results are summarized in the following Table.

TABLE 18

Molecular weight and conversion data for poly(vinyl acetate) in the presence of O-ethyl S-cyanomethyl xanthate (73) at 100° C.

| Entry | Reaction time (hr) | $M_n$ | $M_w/M_n$ | % Conversion |
|---|---|---|---|---|
| 1 | 0.5 | 1680 | 1.44 | 3.4 |
| 2 | 1.5 | 11520 | 1.24 | 26.6 |

TABLE 18-continued

Molecular weight and conversion data for poly(vinyl acetate) in the presence of O-ethyl S-cyanomethyl xanthate (73) at 100° C.

| Entry | Reaction time (hr) | $M_n$ | $M_w/M_n$ | % Conversion |
|---|---|---|---|---|
| 3 | 4 | 20977 | 1.39 | 59.7 |
| 4 (Control)* | 1.5 | 61560 | 1.69 | 40.1 |

*In the absence of O-ethyl S-cyanomethyl xanthate.

Example 38

Preparation of Narrow Polydispersity Poly(vinyl Acetate) in the Presence of O-Ethyl S-Cyanomethyl Xanthate (73)

A stock solution comprising of 1,1'-azobis (cyclohexanecarbonitrile) (4 mg), vinyl acetate (10 mL) and O-ethyl S-cyanomethyl xanthate (73) (160.74 mg) in ethyl acetate (10 mL) was prepared. Aliquots (4 mL) of this stock solution were transferred to four separate ampoules. The contents of ampoules were degassed, sealed and heated at 100° C. for specified time. Results are summarized in the following Table.

TABLE 19

Molecular weight and conversion data for poly(vinyl acetate) in the presence of O-ethyl S-cyanomethyl xanthate (73) at 100° C.

| Entry | Reaction time (hr) | $M_n$ | $M_w/M_n$ | % Conversion |
|---|---|---|---|---|
| 1 | 1 | 1440 | 1.23 | 13.2 |
| 2 | 2 | 4600 | 1.16 | 40.7 |
| 3 | 6 | 8420 | 1.34 | 82.3 |
| 4 | 16 | 9095 | 1.37 | 91.7 |

Example 39

Preparation of Narrow Polydispersity Poly(vinyl Acetate) in the Presence of O-Ethyl S-Cyanomethyl Xanthate (73)

A stock solution comprising of 1,1'-azobis (cyclohexanecarbonitrile) 2.12 mg), vinyl acetate (10 mL) and O-ethyl S-cyanomethyl xanthate (73) (160.45 mg), was prepared. Aliquots (2 mL) of this stock solution were transferred to four seperate ampoules. The contents of ampoules were degassed, sealed and heated at 100° C. for specified time. Results are summarized in the following Table

TABLE 20

Molecular weight and conversion data for poly(vinyl acetate) in the presence of O-ethyl S-cyanomethyl xanthate (73) at 100° C.

| Entry | Reaction time (hr) | $M_n$ | $M_w/M_n$ | % Conversion |
|---|---|---|---|---|
| 1 | 1 | 615 | 1.34 | 7.4 |
| 2 | 2 | 2280 | 1.17 | 24.5 |
| 3 | 4 | 7030 | 1.18 | 66.3 |
| 4 | 16 | 10100 | 1.31 | 78.3 |

Example 40

Preparation of Narrow Polydispersity Poly(vinyl Acetate) in the Presence of O-Etyl-S-(2-Cyanoprop-2-yl)xanthate (72)

A stock solution comprising of 1,1'-azobis (cyclohexanecarbonitrile) (2.10 mg), vinyl acetate (12.5 mL) and O-ethyl S-(2-cyanoprop-2-yl)xanthate (72) (23.65 mg) in ethyl acetate (12.5 mL) was prepared. Aliquots (2 mL) of the stock solution were transferred to ampoules. The contents of ampoules were degassed, sealed and heated at 100° C. for specified time. Results are summarized in the following Table.

TABLE 21

Molecular weight and conversion data for poly(vinyl acetate) in the presence of O-ethyl S-(2-cyanopropyl) xanthate (72) at 100° C.

| Entry | Reaction time (hr) | $M_n$ | $M_w/M_n$ | % Conversion |
|---|---|---|---|---|
| 1 | 0.5 | 577 | 1.39 | 1.0 |
| 2 | 1.5 | 3350 | 1.39 | 9.0 |
| 3 | 4 | 19300 | 1.53 | 66.0 |
| 4 | 16 | 20750 | 1.66 | 93.0 |

Example 41

Preparation of Narrow Polydispersity Poly(vinyl Acetate) in the Presence of O-Ethyl S-(2-Ethoxycarbonylprop-2-yl)xanthate (71)

A stock solution comprising of 1,1'-azobis (cyclohexanecarbonitrile) (2.11 mg), vinyl acetate (25 mL) and ethyl acetate (25 mL) was prepared. An aliquot (10 mL) of this solution was transferred to a 10 mL volumetric flask containing O-ethyl S-(2-ethoxycarbonylprop-2-yl)xanthate (71) (29.50 mg) to give a stock solution. Aliquots (2 mL) of this stock solution were then transferred to each of four ampoules. The contents of ampoules were degassed, sealed and heated at 100° C. for the specified time. Results are summarized in the following Table.

TABLE 22

Molecular weight and conversion data for poly(vinyl acetate) in the presence of O-ethyl S-(2-ethoxycarbonylprop-2-yl) xanthate (71) at 100° C.

| Entry | Reaction time (hr) | $M_n$ | $M_w/M_n$ | % Conversion |
|---|---|---|---|---|
| 1 | 0.5 | 1010 | 1.43 | 1.0 |
| 2 | 1.5 | 3170 | 1.39 | 6.5 |
| 3 | 4 | 16100 | 1.22 | 34.0 |
| 4 | 8 | 20750 | 1.52 | 65.5 |

Example 42

Preparation of Narrow Polydispersity Poly(vinyl Acetate) in the Presence of O-Ethyl S-Cyanomethyl Xanthate (73)

A stock solution comprising of 2,2'-azobis (isobutyronitrile) (10.09 mg), vinyl acetate (10 mL) and O-ethyl S-cyanomethyl xanthate (73) (160.89 mg) was prepared. Aliquots (2 mL) of this stock solution were transferred to four seperate ampoules. The contents of ampoules were degassed, sealed and heated at 60° C. for specified time. Results are summarized in the following Table.

TABLE 23

Molecular weight and conversion data for poly(vinyl acetate) in the presence of O-ethyl S-cyanomethyl xanthate (73) at 60° C.

| Entry | Reaction time (hr) | $M_n$ | $M_w/M_n$ | % Conversion |
|---|---|---|---|---|
| 1 | 1 | 326 | 1.30 | 4.2 |
| 2 | 2 | 517 | 1.26 | 6.0 |
| 3 | 4 | 866 | 1.30 | 9.3 |
| 4 | 16 | 11670 | 1.34 | 91.0 |

The following examples show that it is possible to use xanthate esters to control the molecular weight and polydispersity of acrylate ester polymers formed in a batch polymerization process. The lowest polydispersity is obtained with a xanthate which has an electron withdrawing substituent on oxygen (E=E2, G=pentafluorophenyl).

Examples 43, 44

Preparation of Narrow Polydispersity Poly(t-butyl Acrylate) in the Presence of Xanthate Esters A solution comprising the xanthate ester in t-butyl acrylate (3.34 g) and ethyl acetate (6.66 g) and 2,2'-azobis(isobutyronitrile) ($5.445 \times 10^{-2}$ M) was placed in an ampoule which was degassed, sealed and heated at 60° C. for 60 minutes. Results are summarized in the following Table.

TABLE 24

Molecular weight and conversion data for poly(t-butyl acrylate) in the presence of xanthate esters at 60° C.

| Example | Xanthate | [CTA] (mol/L) | [M]/[CTA] | $M_n$ | $M_w/M_n$ | % Conv. |
|---|---|---|---|---|---|---|
| control | — | 0 | 0 | 129174 | 3.7 | >99 |
| 43 | (72) | $2.118 \times 10^{-2}$ | $9.092 \times 10^{-3}$ | 11032 | 1.77 | 71.5 |
| 44 | (75) | $2.148 \times 10^{-2}$ | $9.219 \times 10^{-3}$ | 11247 | 1.40 | 81.3 |

Example 45

Styrene Polymerization Using O-Pentafluorophenyl-S-benzyl Xanthate (75) and O-Phenyl-S-benzyl Xanthate (74)

Solutions I, of O-pentafluorophenyl-S-benzyl xanthate (75) (51.36 mg) in 5 mL of styrene, and II, O-phenyl-S-benzyl xanthate (74) (22.92 mg) in 3 mL of styrene were prepared. 2 mL aliquots of solution I were transferred to each of two ampoules which were degassed, sealed and heated at 110° C. for 6 and 20 hours. A 2 mL aliquot of the solution II was transferred to an ampoule, degassed, sealed and heated at 110° C. for 6 hours. The respective polymers were analysed by GPC after removal of excess monomer.

TABLE 25

Molecular weight and conversion data for polystyrene prepared in the presence of xanthates (75) and (74) at 110° C.

| Entry | Xanthate | Time/hr | $M_n$ | $M_w/M_n$ | % Conv. |
|---|---|---|---|---|---|
| 1 | (74) | 6 | 23 698 | 1.60 | 24.6 |
| 2 | (75) | 6 | 14 097 | 1.53 | 23.7 |
| 3 | (75) | 20 | 18 862 | 1.48 | 57.9 |

Example 46

Methyl Acrylate Polymerization in the Presence of O-Pentafluorophenyl-S-benzylxanthate (75) and O-Phenyl-S-benzylxanthate (74)

Stock solutions I, comprising 2,2'-azobis(isobutyronitrile) (3.75 mg) in 25 mL of benzene, II, comprising O-phenyl-S-benzylxanthate (39.00 mg) in 2 mL of methyl acrylate, and III, comprising O-pentafluorophenyl-S-benzylxanthate (78.75 mg) in 3 mL of methyl acrylate were prepared. 4 mL aliquots of stock solution I were transferred to each of three ampoules. A 1 mL aliquot of stock solution II was transferred to one of the above ampoules which was degassed, sealed and heated at 60° C. for 4 hours. 1 mL aliquots of stock solution III were transferred to the two remaining ampoules which were degassed, sealed and heated at 60° C. for 4 and 16 hours. The respective polymers were analysed by GPC after removal of excess monomer.

TABLE 26

Molecular weight and conversion data for poly(methyl acrylate) prepared in the presence of dithio-compounds at 60° C.

| Entry | Dithio compound | Time/hr | $M_n$ | $M_w/M_n$ | % Conv. |
|---|---|---|---|---|---|
| 1 | (74) | 4 | 15 450 | 1.49 | 54.3 |
| 2 | (75) | 4 | 12 049 | 1.47 | 48.7 |
| 3 | (75) | 16 | 14 806 | 1.43 | 85.6 |

The following examples demonstrate the use of vinylogous dithioesters in the synthesis of narrow polydispersity polymers.

Example 47

Polymerization of Styrene in the Presence of 3-Benzylthio-5,5-dimethylcyclohex-2-ene-1-thione (30)

The vinylogous dithioester, 3-Benzylthio-5,5-dimethylcyclohex-2-ene-1-thione (30) (40.5 mg; 0.154 mmol) was dissolved in styrene (5.0 g) (concentration of (17)=0.028M). The solution was equally dispensed into two ampoules which were degassed and heated in an oil bath at 110° C. for 6 and 16 hrs.

TABLE 27

Molecular weight and conversion data for polystyrene prepared by thermal polymerization of styrene in the presence of (30) at 110° C.

| Entry | Time (h) | $\overline{M}_n$ | $\overline{M}_w/\overline{M}_n$ | % conv. |
|---|---|---|---|---|
| 1 | 6 | 5528 | 1.16 | 10.3 |
| 2 | 16 | 16561 | 1.35 | 25.1 |

Example 48

Thermal Polymerization of Styrene in the Presence of (76)

A stock solution of the CTA (76) (64.1 mg) in styrene (5 mL) was prepared. Two 2 mL aliquots of this solution were transferred to ampoules which were degassed, sealed and heated at 100° C. for the times indicated. The volatiles were removed under reduced pressure and the residues dried to constant weight. The polymers were analyzed by GPC.

TABLE 28

Molecular weight and conversion data for polystyrene prepared by thermal polymerization of styrene in the presence of (76) at 100° C.

| Entry | Time (h) | $\overline{M}_n$ | $\overline{M}_w/\overline{M}_n$ | % conv. |
|---|---|---|---|---|
| 1 | 6 | 2393 | 1.23 | 9.8 |
| 2 | 64 | 20982[a] | 1.54 | 87.7 |

[a]bimodal molecular weight distribution.

Example 49

Methyl Acrylate Polymerization in the Presence of Benzyl 3,3-(Dibenzylthio)propenedithioate (76)

A solution of the CTA (76) (105 mg), 2,2'-azobis(isobutyronitrile) (1.8 mg) and methyl acrylate (3 mL) in benzene (12 mL) was prepared. Two 5 mL aliquots of this solution were transferred to ampoules, degassed, sealed and heated at 60° C. for 8 and 16 hours respectively. The resulting polymers were analysed by GPC after the removal of excess monomer and solvent.

TABLE 29

Molecular weight and conversion data poly(methyl acrylate) prepared in the presence of benzyl 3,3-(dibenzylthio)propenedithioate (76) using 2,2'-azobis(isobutyronitrile) as initiator at 60° C.

| Example | Time (h) | $\overline{M}_n$ | $\overline{M}_w/\overline{M}_n$ | % conv. |
|---|---|---|---|---|
| 1 | 8 | 2714 | 1.22 | 6.2% |
| 2 | 16 | 6390 | 1.11 | 9.6% |

Example 50

MMA Polymerization Using 2-Cyanoprop-2-yl-1-pyrrolecarbodithioate (63)

Stock solutions I, comprising 2,2'-azobis(isobutyronitrile) (24.03 mg) in 5 mL of benzene, and II, comprising 2-cyanoprop-2-yl-1-pyrrolecarbodithioate (156.28 mg) in 5 mL of MMA were prepared. 0.5 mL aliquots of stock solution I were transferred to each of four ampoules. An aliquot of 1.5 mL of MMA was transferred to one of the above ampoules, degassed, sealed and heated at 60° C. for 2 hours (control). Three 1.5 mL aliquots of stock solution II were transferred to the three remaining ampoules, degassed, sealed and heated at 60° C. for 2, 4, 8 hours. The respective polymers were analysed by GPC after removal of excess monomer.

TABLE 30

Molecular weight and conversion data for poly(methyl methacrylate) prepared in the presence of dithicarbamate (63) at 60° C.

| Entry | Time/hr | $M_n$ | $M_w/M_n$ | % Conv. |
|---|---|---|---|---|
| 1[a] | 2 | 274 929 | 1.67 | 23.6 |
| 2 | 2 | 3 986 | 1.35 | 26.0 |
| 3 | 4 | 4 992 | 1.28 | 53.3 |
| 4 | 8 | 6 717 | 1.18 | 85.7 |

[a]Contol, no added dithiocarbamate

The following example illustrates the synthesis of a narrow polydispersity block copolymer.

Example 51

Preparation of Low Polydispersity Poly(methyl Methacrylate-block-styrene)

Poly(methyl Methacrylate) ($M_n$ 6,717, $M_w/M_n$ 1.18) was prepared under the conditions described in example 49. A stock solution comprising 2,2'-azobis(isobutyronitrile) (4.5 mg) in 15 mL of styrene was prepared and the abovementioned poly(methyl methacrylate) (840 mg) was dissolved in 12 mL of this solution. An aliquot of 10 mL of the styrene, PMMA and 2,2'-azobis(isobutyronitrile) mixture was transferred to an ampoule, degassed sealed and heated at 60° C. for 20 hours. The resulting polymer was analyzed by GPC after removal of excess monomer. The block copolymer had $M_n$ 25 609, $M_w/M_n$ 1.15 (conversion 26.8%).

The following example illustrates the synthesis of a narrow polydispersity copolymer.

Example 52

Preparation of Low Polydispersity Poly(t-butyl Acrylate-co-vinyl Acetate)

A stock solution comprising of 1,1'-azobis(cyclohexanecarbonitrile) (2.30 mg), vinyl acetate (9.34 g) and was prepared. An aliquot (400 ml) of the stock solution was added to an ampoule containing t-butyl acrylate (200 ml) and O-pentafluorophenyl-S-benzylxanthate (75) (10.2 mg). The ampoule was degassed, sealed and heated at 100° C. for 16 hours. The resulting polymer was analysed by GPC after removal of excess monomer. The copolymer had Mn 16517, $M_w/M_n$ 1.31 (conversion 68%).

The following examples illustrate vinyl acetate polymerization in the presence of a conventional chain transfer agent. Polydispersities are strongly dependent on the particular chain transfer agent and its concentration. Where chain transfer constants are high (e.g. a with thiol) broad polydispersities are obtained. Compare example 42 where narrow polydispersities are retained throughout the course of the polymerization to >90% conversion.

Comparative Example 1

Polymerization of Vinyl Acetate in the Presence Carbon Tetrachloride

A stock solution of 2,2'-azobis(isobutyronitrile) (8.3 mg) in vinyl acetate (50 mL) was prepared. Aliquots (10 mL) of this solution were transferred to ampoules containing various amounts of $CCl_4$ as shown in Table. The contents of ampoules were degassed, sealed and heated at 60° C. for one hour.

TABLE 31

Molecular weight and conversion date for poly(vinyl acetate) prepared in the presence of carbon tetrachloride as chain transfer agent:

| Entry | $CCl_4$ (g) | $[CCl_4]/[VAc]$ | $M_n$ | $M_w/M_n$ | % Conv. |
|---|---|---|---|---|---|
| 1 (control) | 0 | 0 | 106350 | 1.9 | 13.1 |
| 2 | 0.16 | 0.00958 | 9800 | 1.8 | 9.3 |
| 3 | 0.32 | 0.01917 | 5200 | 1.8 | 10.5 |
| 4 | 0.64 | 0.03834 | 2600 | 1.8 | 10.8 |

Analysis of the data via a Mayo plot shows that the transfer constant of carbon tetrachloride in vinyl acetate polymerization is 0.83.

Comparative Example 2

Polymerization of Vinyl Acetate Using Tert-butyl Mercaptan

Stock solutions (I), of 2,2'-azobis(isobutyronitrile) (14.3 mg) in freshly distilled Vinyl Acetate (50 mL), and (II), comprising tert-butyl mercaptan (20.4 mg) in freshly distilled Vinyl Acetate (10 mL) were prepared. Four separate ampoules were charged with various amounts of stock solutions (I) and (II) to give the indicated concentrations. The ampoules were degassed, sealed and heated at 60° C. for one hour.

TABLE 32

Molecular weight and conversion date for poly(vinyl acetate) prepared in the presence of tert-butyl mercaptan as chain transfer agent:

| Entry | RSH (mg) | [RSH]/[VAc] | $M_n$ | $M_w/M_n$ | % Conv. |
|---|---|---|---|---|---|
| 1 (control) | 0 | 0 | 112300 | 1.8 | 18.7 |
| 2 | 2.04 | 0.00021 | 49680 | 2.9 | 12.3 |
| 3 | 4.08 | 0.00042 | 29950 | 4.3 | 12.1 |
| 4 | 8.16 | 0.00084 | 15000 | 7.5 | 11.9 |

Analysis of the data via a Mayo plot shows that the transfer constant of tert-butyl mercaptan in VAc polymerization is 5.97.

What is claimed is:

1. A process for producing a polymer, said process comprising polymerizing a monomer mix into said polymer in the presence of a source of free radicals and a chain transfer agent having a transfer constant in the range of from 0.1 to 5000, said chain transfer agent having the following formula:

$$S=C\begin{matrix}D\\ \\E\end{matrix}$$

wherein when D is D1 of the following formula:

$$-X=C\begin{bmatrix}S-R\\ \\Z'\end{bmatrix}_p$$

then p is in the range of from 1 to 200, E is Z' and said transfer agent is of the following formula:

$$\begin{bmatrix}S=C\begin{matrix}S\\ \\E\end{matrix}X=C\begin{matrix}S-R\\ \\Z'\end{matrix}\end{bmatrix}_p,$$

wherein when D is D2 of the following formula:

$$-S\frac{}{}_p R$$

then p is in the range of from 1 to 200, E is E1 or E2 and said transfer agent is of the following formula:

$$\begin{bmatrix}S=C\begin{matrix}S-R\\ \\E\end{matrix}\end{bmatrix}_p,$$

wherein when D is D3 of the following formula:

$$-X=C\begin{matrix}S-R^*\\ \\\end{matrix}\frac{}{}_{p'} Z''$$

then p' is in the range of from 2 to 200, E is Z, E1 or E2 and said transfer agent is of the following formula:

$$\begin{bmatrix}S=C\begin{matrix}S\\ \\E\end{matrix}X=C\begin{matrix}S-R^*\\ \\\end{matrix}Z''\end{bmatrix}_{p'}, or$$

wherein when D is D4 of the following formula:

$$-S-R'$$

then E is E3 or E4 and said transfer agent is of the following formula:

$$S=C\begin{matrix}S-R'\\ \\E\end{matrix}$$

where in all of the above:

R is a p-valent moiety derived from a moiety selected from the group consisting of substituted or unsubstituted alkane, substituted or unsubstituted alkene, substituted or unsubstituted arene, unsaturated or aromatic carbocyclic ring, unsaturated or saturated heterocyclic ring, an organometallic species, and a polymer chain, R. being a free radical leaving group resulting from R that initiates free radical polymerization; R* and R' are monovalent moieties independently selected from the group consisting of a substituted or unsubstituted alkyl, substituted or unsubstituted alkenyl, substituted or unsubstituted aryl, unsaturated or aromatic carbocyclic ring, unsaturated or saturated heterocyclic ring, substituted or unsubstituted alkylthio, substituted or unsubstituted alkoxy, substituted or unsubstituted dialkylamino, an organometallic species, and a polymer chain, R*. being a free radical leaving group resulting from R* that initiates free radical polymerization;

X is selected from the group consisting of a substituted or unsubstituted methine, nitrogen, and a conjugating group;

Z' is selected from the group consisting of E1, E2, halogen, substituted or unsubstituted alkyl, substituted or unsubstituted alkenyl, substituted or unsubstituted aryl, substituted or unsubstituted heterocyclyl, substituted or unsubstituted alkylthio, substituted or unsubstituted alkoxycarbonyl, substituted or unsubstituted —COOR", carboxy, substituted or unsubstituted —CONR"$_2$, cyano, —P(=O)(OR")$_2$, —P(=O)R"$_2$; wherein R" is selected from the group consisting of substituted or unsubstituted alkyl, substituted or unsubstituted alkenyl, substituted or unsubstituted aryl, substituted or unsubstituted heterocyclyl, substituted or unsubstituted aralkyl, substituted or unsubstituted alkaryl, and a combination thereof;

Z" is a p'-valent moiety derived from a moiety selected from the group consisting of a substituted or unsubstituted alkane, substituted or unsubstituted alkene, substituted or unsubstituted arene, substituted or unsubstituted heterocycle, a polymer chain, an organometallic species, and a combination thereof;

Z is selected from the group consisting of a halogen, substituted or unsubstituted alkyl, substituted or unsubstituted alkenyl, substituted or unsubstituted aryl, substituted or unsubstituted heterocyclyl, substituted or unsubstituted alkylthio, substituted or unsubstituted alkoxycarbonyl, substituted or unsubstituted —COOR", carboxy, substituted or unsubstituted —CONR"$_2$, cyano, —P(=O)(OR")$_2$, —P(=O)R"$_2$;

E1 is a substituent functionality derived from a substituted or unsubstituted heterocycle attached via a nitrogen atom or is of the following formula:

wherein G and J are independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfonyl, substituted or unsubstituted alkylphosphonyl, substituted or unsubstituted arylsulfonyl, substituted or unsubstituted arylsulfinyl, substituted or unsubstituted arylphosphonyl;

E2 is of the following formula:

wherein G' is selected from the group consisting of substituted or unsubstituted alkenyl, substituted or unsubstituted aryl;

E3 is of the following formula

wherein p'" is between 2 and 200, G" is Z" and J' is independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfonyl, substituted or unsubstituted alkylphosphonyl, substituted or unsubstituted arylsulfonyl, substituted or unsubstituted arylsulfinyl, substituted or unsubstituted arylphosphonyl or is joined to G" so as to form a 5–8 membered ring; and E4 is of the following formula

wherein p'" is between 2 and 200 and G'" is Z'.

2. The process of claim 1 wherein when p'"=1 and D=D1 then E—C—X=C—Z' of said chain transfer agent forms a cyclic structure.

3. The process of claim 2 wherein said chain transfer agent is of the following formula:

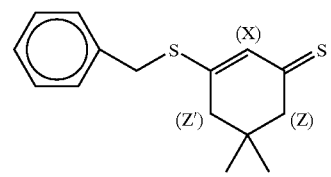

4. The process of claim 1 wherein said functionality derived from said substituted or unsubstituted heterocycle is selected from the group consisting of pyrrole, imidazole, lactam, cyclic imide, indole, carbazole, benzimidazole, benzotriazole, and isatin.

5. The process of claim 1 wherein said chain transfer agent comprises D1 having the following formula:

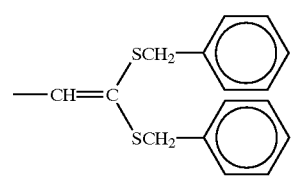

when E1 is of the following formula:

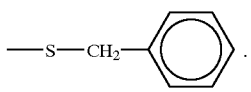

6. The process of claim 1 wherein said chain transfer agent comprises D2 having the following formula:

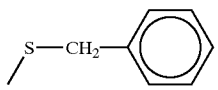

when E1 is of the following formula:

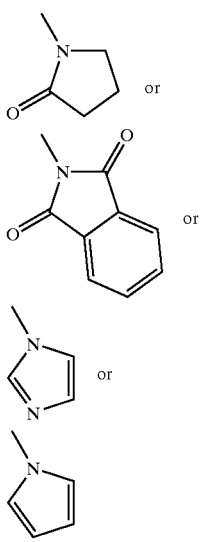

or E2 is of the following formula

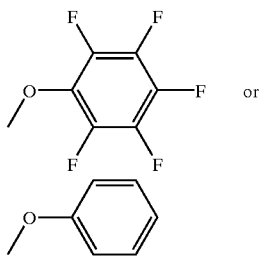

7. The process of claim 1 wherein said chain transfer agent comprises D2 having the following formula:

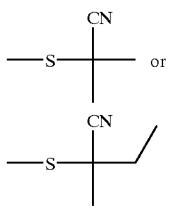

when E1 is of the following formula:

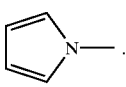

8. The process of claim 1 wherein said chain transfer agent comprises D2 having the following formula:

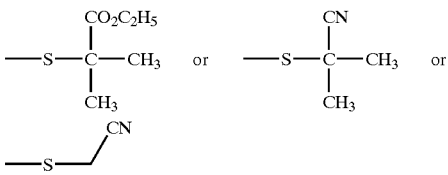

when E2 is of the following formula:

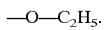

9. The process of claim 1 wherein said monomer mix comprises at least one vinyl monomer having the following formula:

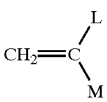

where L is selected from tube group consisting of hydrogen, halogen, and substituted or unsubstituted $C_1$–$C_4$ alkyl, said alkyl substituents being independently selected from the group consisting of hydroxy, alkoxy, OR", $CO_2H$, $O_2CR$", $CO_2R$" and a combination thereof;

where M is selected from the group consisting of hydrogen, R", $CO_2H$, $CO_2R$", COR", CN, $CONH_2$, CONHR", $CONR"_2$, $O_2CR$", OR", and halogen.

10. The process of claim 9 wherein said monomer mix further comprises maleic anhydride, N-alkylmaleimide, N-arylmaleimide, dialkyl fumarate, cyclopolymerizable monomer, a ring opening monomer, a macromonomer or a combination thereof.

11. The process of claim 1 wherein said monomer mix comprises maleic anhydride, N-alkylmaleimide, N-arylmaleimide, dialkyl fumarate, a cyclopolymerizable monomer, a ring-opening monomer or a combination thereof.

12. The process of claim 1 wherein said substituents are independently selected from the group that consists of alkyl, aryl, epoxy, hydroxy, alkoxy, oxo, acyl, acyloxy, carboxy, carboxylate, sulfonic acid, sulfonate, alkoxy- or aryloxy-carbonyl, isocyanato, cyano, silyl, halo, dialkylamino, and amido.

13. The process of claim 1 wherein said process is carried out in a polymerization medium containing said chain transfer agent, said monomer mix and said source of free radicals.

14. The process of claim 13 wherein said free radicals from said source of free radicals are introduced to said polymerization medium after the addition of said chain transfer agent and said monomer mix to said medium.

15. The process of claim 1 wherein said source of free radicals is selected from the group consisting of a thermal initiator, redox initiator, photo initiation system, and a combination thereof.

16. The process of claim 15 wherein said thermal initiator is selected from the group consisting of 2,2'-azobis (isobutyronitrile), 2,2'-azobis(2-cyano-2-butane), dimethyl 2,2'-azobisdimethylisobutyrate, 4,4'-azobis(4-cyanopentanoic acid), 1,1'-azobis(cyclohexanecarbonitrile), 2-(t-butylazo)-2-cyanopropane, 2,2'-azobis[2-methyl-N-(1,1)-bis(hydoxymethyl)-2-hydroxyethyl]propionamide, 2,2'-azobis[2-methyl-N-hydroxyethyl)]-propionamide, 2,2'-azobis(N,N'-dimethyleneisobutyramidine)dihydrochloride, 2,2'-azobis(2-amidinopropane)dihydrochloride, 2,2'-azobis(N,N-dimethyleneisobutyramine), 2,2'-azobis(2-methyl-N-[1,1-bis(hydroxymethyl)-2-hydroxyethyl]propionamide), 2,2'-azobis(2-methyl-N-[1,1-bis(hydroxymethyl)ethyl]propionamide), 2,2'-azobis[2-methyl-N-(2-hydroxyethyl)propionamide], 2,2'-azobis(isobutyramide)dihydrate, 2,2'-azobis(2,2,4-trimethylpentane), 2,2'-azobis(2-methylpropane), t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl hyponitrite, dicumyl hyponitrite and a combination thereof.

17. The process of claim 1 wherein said process is carried out at a polymerization temperature in the range of from −20° C. to 200° C.

18. The process of claim 1 wherein said polymer has a polydispersity in the range of from 1.05 to 1.5.

19. The process of claim 1 wherein said polymer is a dispersed polymer or a solution polymer.

20. A polymer made in accordance with the process of claim 1.

21. A coating composition comprising a polymer made in accordance with the process of claim 1.

22. The process of claim 1 wherein said polymer is of the following formula:

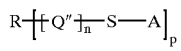

where n is a positive integer in the range of from 1 to 100,000 and wherein A is of the following formula:

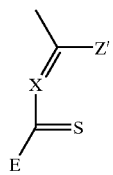

when D is D1 and E is Z';

A is of the following formula:

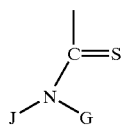

when D is D2 and E is E1; or

A is of the following formula:

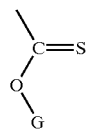

when D is D2 and E is E2; and
and Q" is a repeat unit derived from a monomer selected from the group consisting of maleic anhydride, N-alkylmaleimide, N-arylmaleimide, dialkyl fumarate, cyclopolymerizable monomer, a ring opening monomer, a macromonomer, a vinyl monomer of the following formula:

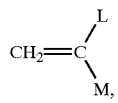

and a combination thereof;
wherein L is selected from the group consisting of hydrogen, halogen, and substituted or unsubstituted $C_1$–$C_4$ alkyl, said alkyl substituents being independently selected from the group consisting of hydroxy, alkoxy, OR", $CO_2H$, $O_2CR$", $CO_2R$" and a combination thereof; and
wherein M is selected from the group consisting of hydrogen, R", $CO_2H$, $CO_2R$", COR", CN, $CONH_2$, CONHR", $CONR"_2$, $O_2CR$", OR", and halogen.

23. The process of claim 1 wherein said polymer is a mixture of isomers of the following formula:

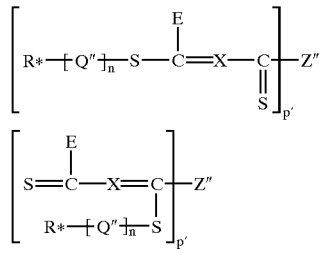

where n is a positive integer in the range of from 1 to 100,000, D is D3, E1 is Z; and Q" is a repeat unit derived from a monomer selected from the group consisting of maleic anhydride, N-alkylmaleimide, N-arylmaleimide, dialkyl fumarate, cyclopolymnerizable monomer, a ring opening monomer, a macromonomer, a vinyl monomer of the following formula:

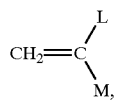

and a combination thereof;
wherein L is selected from the group consisting of hydrogen, halogen, and substituted or unsubstituted $C_1$–$C_4$ alkyl, said alkyl substituents being independently selected from the group consisting of hydroxy, alkoxy, OR", $CO_2H$, $O_2CR$", $CO_2R$" and a combination thereof; and
wherein M is selected from the group consisting of hydrogen, R", $CO_2H$, $CO_2R$", COR", CN, $CONH_2$, CONHR", $CONR"_2$, $O_2CR$", OR", and halogen.

24. The process of claim 1 wherein said polymer is of the following formula:

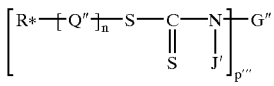

where n is a positive integer in the range of from 1 to 100,000, D is D4, E is E3; and Q" is a repeat unit derived from a monomer selected from the group consisting of maleic anhydride, N-alkylmaleimide, N-arylmaleimide, dialkyl fumarate, cyclopolymerizable monomer, a ring opening monomer, a macromonomer, a vinyl monomer of the following formula:

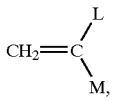

and a combination thereof;
wherein L is selected from the group consisting of hydrogen, halogen, and substituted or unsubstituted $C_1$–$C_4$ alkyl, said alkyl substituents being independently selected from the group consisting of hydroxy, alkoxy, OR", $CO_2H$, $O_2CR"$, $CO_2R"$ and a combination thereof; and
wherein M is selected from the group consisting of hydrogen, R", $CO_2H$, $CO_2R"$, COR", CN, $CONH_2$, CONHR", $CONR"_2$, $O_2CR"$, OR", and halogen.

25. The process of claim 1 wherein said polymer is of the following formula:

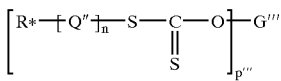

where n is a positive integer in the range of from 1 to 100,000, D is D4, E is E4; and Q" is a repeat unit derived from a monomer selected from the group consisting of maleic anhydride, N-alkylmaleimide, N-arylmaleimide, dialkyl fumarate, cyclopolymerizable monomer, a ring opening monomer, a macromonomer, a vinyl monomer of the following formula:

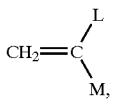

and a combination thereof;
wherein L is selected from the group consisting of hydrogen, halogen, and substituted or unsubstituted $C_1$–$C_4$ alkyl, said alkyl substituents being independently selected from the group consisting of hydroxy, alkoxy, OR", $CO_2H$, $O_2CR"$, $CO_2R"$ and a combination thereof; and
wherein M is selected from the group consisting of hydrogen, R", $CO_2H$, $CO_2R"$, COR", CN, $CONH_2$, CONHR", $CONR"_2$, $O_2CR"$, OR", and halogen.

26. The process of claim 1 wherein said monomer mix comprises vinyl acetate, vinyl butyrate, vinyl benzoate, vinyl chloride, vinyl bromide, vinyl fluoride, N-vinylpyrolidone, N-vinylcarbazole or a combination thereof.

27. The process of claims 1 and 26 wherein D=D2, E=E1 or E2 in said CTA and wherein G, J, and G' are independently selected from the group consisting of substituted or unsubstituted alkyl, substituted or unsubstituted alkene, substituted or unsubstituted aryl, substituted or unsubstituted heterocyclyl, with the proviso that G' is not substituted or unsubstituted alkyl.

28. The process of claim 27 wherein when E=E1, G—N=J form part of a non-aromatic cyclic group.

29. The process of claim 1 wherein said monomer mix comprises a methacrylate, acrylate and styrenic monomers and wherein D=D2, E=E1 and G—N—J forms part of aromatic cyclic group or a non-aromatic cyclic group with substituent conjugated to N.

30. The process of claim 29 where said substituent E1 is substituted or unsubstituted pyrrole, substituted or unsubstituted imidazole, substituted or unsubstituted 2-lactam, substituted or unsubstituted imide.

31. The process of claim 1 and 25 wherein said monomer mix comprises a methacrylate, acrylate, styrenic monomers and a combination thereof, wherein D=D2, E=E2 in said CTA and wherein G' is aryl.

32. The process of claim 31 wherein said aryl is $OC_6H_5$ or $C_6F_6$.

33. A process for producing a polymer, said process comprising: charging a polymerization medium in a reactor with a chain transfer agent; introducing a source of free radicals and a monomer mix into said medium to polymerize said monomer mix into said polymer, said chain transfer agent having a transfer constant in the range of from 0.1 to 5000 and having the following formula:

wherein when D is D1 of the following formula:

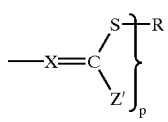

then p is in the range of from 1 to 200, E is Z' and said transfer agent is of the following formula:

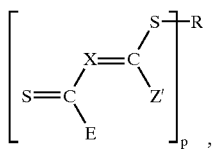

wherein when D is D2 of the following formula:

then p is in the range of from 1 to 200, E is E1 or E2 and said transfer agent is of the following formula:

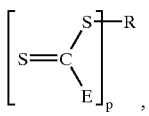

wherein when D is D3 of the following formula:

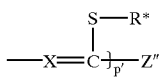

then p' is in the range of from 2 to 200, E is Z, E1 or E2 and said transfer agent is of the following formula:

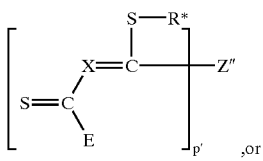

wherein when D is D4 of the following formula:

then E is E3 or E4 and said transfer agent is of the following formula:

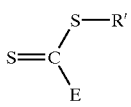

where in all of the above:

R is a p-valent moiety derived from a moiety selected from the group consisting of substituted or unsubstituted alkane, substituted or unsubstituted alkene, substituted or unsubstituted arene, unsaturated or aromatic carbocyclic ring, unsaturated or saturated heterocyclic ring, an organometallic species, and a polymer chain, R. being a free radical leaving group resulting from R that initiates free radical polymerization;

R* and R' are monovalent moieties independently selected from the group consisting of a substituted or unsubstituted alkyl, substituted or unsubstituted alkenyl, substituted or unsubstituted aryl, unsaturated or aromatic carbocyclic ring, unsaturated or saturated heterocyclic ring, substituted or unsubstituted alkylthio, substituted or unsubstituted alkoxy, substituted or unsubstituted dialkylamino, an organometallic species, and a polymer chain, R*. being a free radical leaving group resulting from R* that initiates free radical polymerization;

X is selected from the group consisting of a substituted or unsubstituted methine, nitrogen, and a conjugating group;

Z' is selected from the group consisting of E1, E2, halogen, substituted or unsubstituted alkyl, substituted or unsubstituted alkenyl, substituted or unsubstituted aryl, substituted or unsubstituted heterocyclyl, substituted or unsubstituted alkylthio, substituted or unsubstituted alkoxycarbonyl, substituted or unsubstituted —COOR", carboxy, substituted or unsubstituted —CONR"$_2$, cyano, —P(=O)(OR")$_2$, —P(=O)R"$_2$;

R" is selected from the group consisting of substituted or unsubstituted alkyl, substituted or unsubstituted alkenyl, substituted or unsubstituted aryl, substituted or unsubstituted heterocyclyl, substituted or unsubstituted aralkyl, substituted or unsubstituted alkaryl, and a combination thereof;

Z" is a p'-valent moiety derived from a moiety selected from the group consisting of a substituted or unsubstituted alkane, substituted or unsubstituted alkene, substituted or unsubstituted arene, substituted or unsubstituted heterocycle, a polymer chain, an organometallic species, and a combination thereof;

Z is selected from the group consisting of a halogen, substituted or unsubstituted alkyl, substituted or unsubstituted alkenyl, substituted or unsubstituted aryl, substituted or unsubstituted heterocyclyl, substituted or unsubstituted alkylthio, substituted or unsubstituted alkoxycarbonyl, substituted or unsubstituted —COOR", carboxy, substituted or unsubstituted —CONR"$_2$, cyano, —P(=O)(OR")$_2$, —P(=O)R"$_2$;

E1 is a substituent functionality derived from a substituted or unsubstituted heterocycle attached via a nitrogen atom, or is of the following formula:

wherein G and J are independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfinyl, substituted or unsubstituted alkylphosphonyl, substituted or unsubstituted arylsulfonyl, substituted or unsubstituted arylsulfinyl, substituted or unsubstituted arylphosphonyl;

E2 is of the following formula:

wherein G' is selected from the group consisting of substituted or unsubstituted alkenyl, substituted or unsubstituted aryl;

E3 is of the following formula

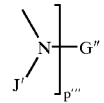

wherein p'" is between 2 and 200, G" is Z" and J' is independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfinyl, substituted or unsubstituted alkylphosphonyl, substituted or unsubstituted arylsulfonyl, substituted or unsubstituted arylsulfinyl, substituted or E4 is of the following formula

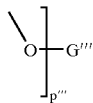

wherein p''' is between 2 and 200 and G''' is Z''.

said monomer mix comprising one or more monomers selected from the group consisting of maleic anhydride, N-alkylmaleimide, N-arylmaleimide, dialkyl fumarate, cyclopolymerizable monomer, and vinyl monomer having the formula:

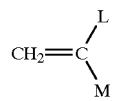

where L is selected from the group consisting of hydrogen, halogen, and substituted or unsubstituted $C_1$-$C_4$ alkyl, said alkyl substituents being independently selected from the group consisting of hydroxy, alkoxy, OR'', $CO_2H$, $O_2CR''$, $CO_2R''$ and a combination thereof;

where M is selected from the group consisting of hydrogen, R'', $CO_2H$, $CO_2R''$, COR'', CN, $CONH_2$, CONHR'', $CONR''_2$, $O_2CR''$, OR'', and halogen.

34. A chain transfer agent having a transfer constant in the range of from 0.1 to 5000, said chain transfer agent having the following formula:

wherein when D is D1 of the following formula:

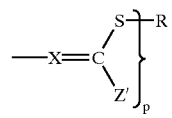

then p is in the range of from 1 to 200, E is Z' and said transfer agent is of the following formula:

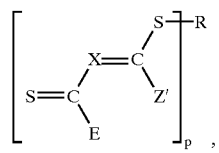

wherein when D is D2 of the following formula:

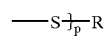

then p is in the range of from 1 to 200, E is E1 or E2 and said transfer agent is of the following formula:

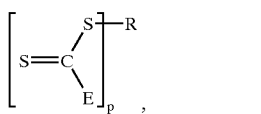

wherein when D is D3 of the following formula:

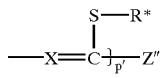

then p' is in the range of from 2 to 200, E is Z, E1 or E2 and said transfer agent is of the following formula:

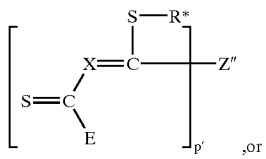

wherein when D is D4 of the following formula:

then E is E3 or E4 and said transfer agent is of the following formula:

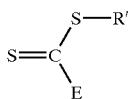

where in all of the above:

R is a p-valent moiety derived from a moiety selected from the group consisting of substituted or unsubstituted alkane, substituted or unsubstituted alkene, substituted or unsubstituted arene, unsaturated or aromatic carbocyclic ring, unsaturated or saturated heterocyclic ring, an organometallic species, and a polymer chain, R. being a free radical leaving group resulting from R that initiates free radical polymerization;

R* and R' are monovalent moieties independently selected from the group consisting of a substituted or unsubstituted alkyl, substituted or unsubstituted alkenyl, substituted or unsubstituted aryl, unsaturated or aromatic carbocyclic ring, unsaturated or saturated heterocyclic ring, substituted or unsubstituted alkylthio, substituted or unsubstituted alkoxy, substituted or unsubstituted dialkyl amino, an organometallic species, and a polymer chain, R*• being a free radical leaving group resulting from R* that initiates free radical polymerization;

X is selected from the group consisting of a substituted or unsubstituted methine, nitrogen, and a conjugating group;

Z' is selected from the group consisting of E1, E2, halogen, substituted or unsubstituted alkyl, substituted or unsubstituted alkenyl, substituted or unsubstituted aryl, substituted or unsubstituted heterocyclyl, substituted or unsubstituted alkylthio, substituted or unsubstituted alkoxycarbonyl, substituted or unsubstituted —COOR'', carboxy, substituted or unsubstituted —CONR''$_2$, cyano, —P(=O)(OR'')$_2$, —P(=O)R''$_2$;

R" is selected from the group consisting of substituted or unsubstituted alkyl, substituted or unsubstituted alkenyl, substituted or unsubstituted aryl, substituted or unsubstituted heterocyclyl, substituted or unsubstituted aralkyl, substituted or unsubstituted alkaryl, and a combination thereof;

Z" is a p'-valent moiety derived from a moiety selected from the group consisting of a substituted or unsubstituted alkane, substituted or unsubstituted alkene, substituted or unsubstituted arene, substituted or unsubstituted heterocycle, a polymer chain, an organometallic species, and a combination thereof;

Z is selected from the group consisting of a halogen, substituted or unsubsfituted alkyl, substituted or unsubstituted alkenyl, substituted or unsubstituted aryl substituted or unsubstituted heterocyclyl, substituted or unsubstituted alkylthio, substituted or unsubstituted alkoxycarbonyl, substituted or unsubstituted —COOR", carboxy, substituted or unsubstituted —CONR"$_2$, cyano, —P(=O)(OR")$_2$, —P(=O)R"$_2$;

E1 is a substituent functionality derived from a substituted or unsubstituted heterocycle attached via a nitrogen atom, or is of the following formula:

wherein G and J are independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfinyl, substituted or unsubstituted alkylphosphonyl, substituted or unsubstituted arylsulfonyl, substituted or unsubstituted arylsulfinyl, substituted or unsubstituted arylphosphonyl;

E2 is of the following formula:

wherein G' is selected from the group consisting of substituted or unsubstituted alkenyl, substituted or unsubstituted aryl;

E3 is of the following formula

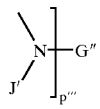

wherein p'" is between 2 and 200, G" is Z" and J' is independently selected from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkenyl, substituted or unsubstituted alkylsulfonyl, substituted or unsubstituted alkylsulfinyl, substituted or unsubstituted alkylphosphonyl, substituted or unsubstituted arylsulfonyl, substituted or unsubstituted arylsulfinyl, substituted or unsubstituted arylphosphonyl or is joined to G" so as to form a 5–8 membered ring; and E4 is of the following formula

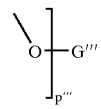

wherein p'" is between 2 and 200 and G'" is Z", with the provisos that when D is D2, p=1 and R' is benzyl or ring substituted benzyl and E is E1 then G and J are not both alkyl, when D is D2, p=1 and R' is benzyl and E is E2 then G' is not alkyl, when D is D2, p=2 and R is p-xylylene and E is E1 then G and J are not hydrogen, substituted or unsubstituted alkyl, substituted or unsubstituted aryl, and when D is D2, p=2 to 12 and R is (—CH$_2$)$_p$Y where Y is p-valent moiety and E is E1 then G and J are not substituted or unsubstituted alkyl, substituted or unsubstituted aryl.

35. The chain transfer agent of claim 34 where D2 is of the following formula:

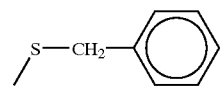

when E is E1 or E2, wherein E1 is of the following formula:

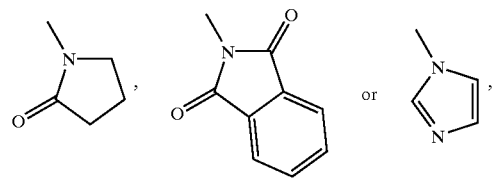

and E2 is of the following formula:

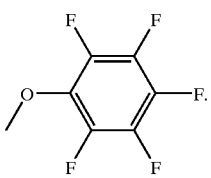

36. The chain transfer agent of claim 34 where D2 is of the following formula:

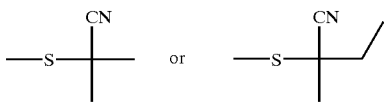

when E1 is of the following formula:

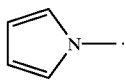

37. The chain transfer agent of claim 34 where D2 is of the following formula:

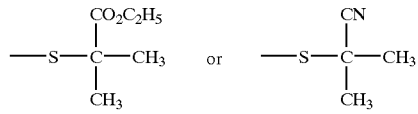

when E2 is of the following formula:

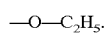

38. The process of claim 1 wherein said polymer a block or gradient copolymer produced by sequentially adding monomers.

39. The chain transfer agent of claim 34 where D is D2 when E is E1 or E2, wherein E1 is of the following formula:

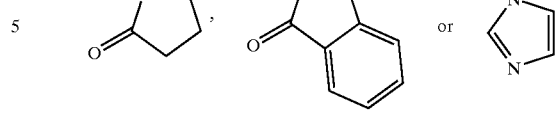

and E2 is of the following formula:

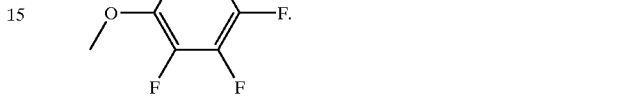

40. The chain transfer agent of claim 34 where D is D2 when E1 is of the following formula:

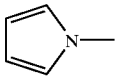

with the proviso that R is not benzyl.

* * * * *

UNITED STATES PATENT AND TRADEMARK OFFICE
CERTIFICATE OF CORRECTION

PATENT NO. : 6,642,318 B1
DATED : November 4, 2003
INVENTOR(S) : Chiefari, John et al.

It is certified that error appears in the above-identified patent and that said Letters Patent is hereby corrected as shown below:

Column 56,
Line 30, delete the word "tube" between the words "from group" insert -- the --

Column 58,
Line 46, "E1" should be -- E --.
Line 49, "cyclopolymnerizable" should be -- cyclopolymerizable --.

Column 63,
Line 4, after the words "substituted or" add the words -- unsubstituted arylphosphonyl or is joined to G" so as to form a 5-8 membered ring; and --

Column 65,
Line 14, "unsubsfituted" should read -- unsubstituted --

Signed and Sealed this

Twentieth Day of July, 2004

JON W. DUDAS
*Acting Director of the United States Patent and Trademark Office*